United States Patent
Hjelmgaard et al.

(10) Patent No.: US 12,397,537 B2
(45) Date of Patent: Aug. 26, 2025

(54) FIRE-PROTECTING INSULATION PRODUCT AND USE OF SUCH PRODUCT

(71) Applicant: Rockwool A/S, Hedehusene (DK)

(72) Inventors: Thomas Hjelmgaard, Fredensborg (DK); Thomas Tielemann, Vreden (DE)

(73) Assignee: Rockwool A/S, Hedehusene (DK)

( * ) Notice: Subject to any disclaimer, the term of this patent is extended or adjusted under 35 U.S.C. 154(b) by 0 days.

(21) Appl. No.: 16/611,321

(22) PCT Filed: Nov. 13, 2017

(86) PCT No.: PCT/EP2017/079090
§ 371 (c)(1),
(2) Date: Nov. 6, 2019

(87) PCT Pub. No.: WO2018/206131
PCT Pub. Date: Nov. 15, 2018

(65) Prior Publication Data
US 2020/0165399 A1    May 28, 2020

(30) Foreign Application Priority Data

May 11, 2017 (WO) .................. PCT/EP2017/061418
May 11, 2017 (WO) .................. PCT/EP2017/061419

(51) Int. Cl.
*B32B 37/12* (2006.01)
*B32B 5/12* (2006.01)
(Continued)

(52) U.S. Cl.
CPC .............. *B32B 37/12* (2013.01); *B32B 5/12* (2013.01); *B32B 5/26* (2013.01); *B32B 7/12* (2013.01); *B32B 15/14* (2013.01); *B32B 19/04* (2013.01); *B32B 19/041* (2013.01); *B32B 37/1207* (2013.01); *B32B 37/18* (2013.01); *B32B 38/0004* (2013.01); *C03C 13/06* (2013.01); *C03C 25/26* (2013.01); *C03C 25/32* (2013.01);
(Continued)

(58) Field of Classification Search
None
See application file for complete search history.

(56) References Cited

U.S. PATENT DOCUMENTS 3,411,972 A   11/1968 Salyer et al.
4,613,627 A    9/1986 Sherman et al.
(Continued)

FOREIGN PATENT DOCUMENTS

DE    4130077 A1    3/1993
EP    1184033 A1    3/2002
(Continued)

OTHER PUBLICATIONS

AAK Handbook Vegetable Oils and Fats, 2007, AAK, Denmark, second ed.*
(Continued)

*Primary Examiner* — Jennifer A Gillett
(74) *Attorney, Agent, or Firm* — Dinsmore & Shohl LLP

(57) ABSTRACT

A fire-protecting insulation product has air-laid mineral wool fibres and a binder. The binder is the result of curing a binder composition comprising at least one hydrocolloid. The product further comprises a particulate endothermic material.

27 Claims, 3 Drawing Sheets

(51) Int. Cl.

| | |
|---|---|
| *B32B 5/26* | (2006.01) |
| *B32B 7/12* | (2006.01) |
| *B32B 15/14* | (2006.01) |
| *B32B 19/04* | (2006.01) |
| *B32B 37/14* | (2006.01) |
| *B32B 37/18* | (2006.01) |
| *B32B 38/00* | (2006.01) |
| *C03C 13/06* | (2006.01) |
| *C03C 25/26* | (2018.01) |
| *C03C 25/32* | (2018.01) |
| *C03C 25/321* | (2018.01) |
| *C03C 25/328* | (2018.01) |
| *C08J 5/04* | (2006.01) |
| *C08L 1/28* | (2006.01) |
| *C08L 3/02* | (2006.01) |
| *C08L 5/12* | (2006.01) |
| *C08L 89/06* | (2006.01) |
| *C09J 5/00* | (2006.01) |
| *C09J 11/06* | (2006.01) |
| *C09J 101/28* | (2006.01) |
| *C09J 103/02* | (2006.01) |
| *C09J 105/00* | (2006.01) |
| *C09J 105/04* | (2006.01) |
| *C09J 105/06* | (2006.01) |
| *C09J 105/12* | (2006.01) |
| *C09J 189/00* | (2006.01) |
| *C09J 189/06* | (2006.01) |
| *D04H 1/413* | (2012.01) |
| *D04H 1/4209* | (2012.01) |
| *D04H 1/4218* | (2012.01) |
| *D04H 1/4266* | (2012.01) |
| *D04H 1/587* | (2012.01) |
| *D04H 1/593* | (2012.01) |
| *D04H 1/64* | (2012.01) |
| *D04H 1/724* | (2012.01) |
| *D04H 1/74* | (2006.01) |
| *D04H 3/002* | (2012.01) |
| *D04H 3/004* | (2012.01) |
| *E04B 1/74* | (2006.01) |
| *E04B 1/80* | (2006.01) |
| *E04B 1/88* | (2006.01) |
| *E04B 1/94* | (2006.01) |
| *E04C 2/284* | (2006.01) |
| *E04D 3/35* | (2006.01) |
| *E04F 13/08* | (2006.01) |
| *C12N 9/02* | (2006.01) |
| *C12N 9/06* | (2006.01) |
| *C12N 9/08* | (2006.01) |
| *C12N 9/10* | (2006.01) |
| *C12N 9/90* | (2006.01) |
| *E04B 1/76* | (2006.01) |

(52) U.S. Cl.
CPC .......... *C03C 25/321* (2013.01); *C03C 25/328* (2013.01); *C08J 5/043* (2013.01); *C08L 1/286* (2013.01); *C08L 3/02* (2013.01); *C08L 5/12* (2013.01); *C08L 89/06* (2013.01); *C09H 11/00* (2013.01); *C09J 5/00* (2013.01); *C09J 11/06* (2013.01); *C09J 101/28* (2013.01); *C09J 101/286* (2013.01); *C09J 103/02* (2013.01); *C09J 105/00* (2013.01); *C09J 105/04* (2013.01); *C09J 105/06* (2013.01); *C09J 105/12* (2013.01); *C09J 189/005* (2013.01); *C09J 189/06* (2013.01); *D04H 1/413* (2013.01); *D04H 1/4209* (2013.01); *D04H 1/4218* (2013.01); *D04H 1/4266* (2013.01); *D04H 1/587* (2013.01); *D04H 1/593* (2013.01); *D04H 1/64* (2013.01); *D04H 1/724* (2013.01); *D04H 1/74* (2013.01); *D04H 3/002* (2013.01); *D04H 3/004* (2013.01); *E04B 1/74* (2013.01); *E04B 1/80* (2013.01); *E04B 1/88* (2013.01); *E04B 1/94* (2013.01); *E04C 2/284* (2013.01); *E04D 3/352* (2013.01); *E04F 13/0866* (2013.01); *B32B 2037/1215* (2013.01); *B32B 2037/1253* (2013.01); *B32B 2037/1269* (2013.01); *B32B 38/164* (2013.01); *B32B 2250/20* (2013.01); *B32B 2250/40* (2013.01); *B32B 2255/02* (2013.01); *B32B 2255/26* (2013.01); *B32B 2262/108* (2013.01); *B32B 2305/20* (2013.01); *B32B 2305/72* (2013.01); *B32B 2307/304* (2013.01); *B32B 2307/732* (2013.01); *B32B 2309/02* (2013.01); *B32B 2315/14* (2013.01); *B32B 2317/00* (2013.01); *B32B 2419/06* (2013.01); *B32B 2607/00* (2013.01); *C03C 2213/00* (2013.01); *C03C 2218/11* (2013.01); *C08J 2301/28* (2013.01); *C08J 2303/02* (2013.01); *C08J 2389/06* (2013.01); *C08J 2405/00* (2013.01); *C08J 2405/04* (2013.01); *C08J 2405/06* (2013.01); *C08J 2405/12* (2013.01); *C08J 2491/00* (2013.01); *C08J 2493/00* (2013.01); *C08L 2201/52* (2013.01); *C08L 2205/03* (2013.01); *C09J 2400/146* (2013.01); *C09J 2401/00* (2013.01); *C09J 2403/00* (2013.01); *C09J 2405/00* (2013.01); *C09J 2489/00* (2013.01); *C12N 9/0022* (2013.01); *C12N 9/0051* (2013.01); *C12N 9/0059* (2013.01); *C12N 9/0065* (2013.01); *C12N 9/0071* (2013.01); *C12N 9/1044* (2013.01); *C12N 9/90* (2013.01); *C12Y 104/03013* (2013.01); *C12Y 108/03002* (2013.01); *C12Y 110/03001* (2013.01); *C12Y 111/01007* (2013.01); *C12Y 114/18001* (2013.01); *C12Y 203/01013* (2013.01); *C12Y 203/02013* (2013.01); *C12Y 503/04001* (2013.01); *D10B 2505/20* (2013.01); *E04B 2001/742* (2013.01); *E04B 2001/743* (2013.01); *E04B 2001/745* (2013.01); *E04B 2001/7683* (2013.01)

(56) References Cited

U.S. PATENT DOCUMENTS

| | | |
|---|---|---|
| 2003/0181114 A1 | 9/2003 | Newton et al. |
| 2007/0027281 A1 | 2/2007 | Michl et al. |
| 2007/0142596 A1 | 6/2007 | Swift et al. |
| 2009/0170978 A1* | 7/2009 | Kelly ................. C08L 3/02 524/72 |
| 2010/0170299 A1* | 7/2010 | Hansen ............ D04H 1/4218 65/442 |
| 2010/0236972 A1* | 9/2010 | Aoki .................. A47G 19/00 523/128 |
| 2010/0282996 A1 | 11/2010 | Jaffrennou et al. |
| 2010/0330376 A1* | 12/2010 | Trksak .................. C08L 83/00 428/426 |
| 2011/0003522 A1* | 1/2011 | Chen ................. C09J 189/00 252/62 |
| 2011/0054098 A1 | 3/2011 | Tutin et al. |
| 2011/0086567 A1 | 4/2011 | Hawkins et al. |
| 2011/0189479 A1* | 8/2011 | Zhang ................. C09J 133/02 428/375 |
| 2011/0190425 A1 | 8/2011 | Swift |
| 2011/0200814 A1 | 8/2011 | Hernandez-Torres et al. |
| 2011/0230111 A1 | 9/2011 | Weir et al. |

(56) References Cited

U.S. PATENT DOCUMENTS

| | | |
|---|---|---|
| 2011/0262648 A1 | 10/2011 | Lee et al. |
| 2011/0263757 A1 | 10/2011 | Rand et al. |
| 2011/0306726 A1* | 12/2011 | Bailey ............... C09J 161/32 524/598 |
| 2012/0037836 A1* | 2/2012 | Hansen ............. C09D 179/02 252/62 |
| 2012/0207907 A1 | 8/2012 | Lanter |
| 2013/0140481 A1* | 6/2013 | Naerum ............. C09J 179/08 252/62 |
| 2014/0083328 A1* | 3/2014 | Lochel, Jr. ........... D04H 3/12 106/162.8 |
| 2014/0134909 A1 | 5/2014 | Guo et al. |
| 2014/0141057 A1 | 5/2014 | Wibaux et al. |
| 2015/0048554 A1* | 2/2015 | Karrer ................ B29C 48/022 264/494 |
| 2015/0087783 A1 | 3/2015 | Zhang et al. |
| 2016/0214890 A1 | 7/2016 | Savonnet et al. |
| 2016/0312941 A1 | 10/2016 | Alavi et al. |
| 2019/0135688 A1 | 5/2019 | Hjelmgaard |
| 2022/0189478 A1 | 6/2022 | Boo |

FOREIGN PATENT DOCUMENTS

| | | | |
|---|---|---|---|
| EP | 2738232 A1 | 6/2014 | |
| EP | 2990494 A1 | 3/2016 | |
| EP | 3187474 A1 | 7/2017 | |
| SU | 1025705 A1 | 6/1983 | |
| WO | 97019141 A1 | 5/1997 | |
| WO | 1997/20780 | 6/1997 | |
| WO | 1999/51536 | 10/1999 | |
| WO | WO-9952988 A1 * | 10/1999 | ........... A61L 24/106 |
| WO | 2000/17121 A1 | 3/2000 | |
| WO | 2007/014236 A2 | 2/2007 | |
| WO | 2007/020065 A1 | 2/2007 | |
| WO | 2009/080696 A2 | 7/2009 | |
| WO | 2009/080938 A2 | 7/2009 | |
| WO | 2010132641 A1 | 11/2010 | |
| WO | WO-2010125163 A1 * | 11/2010 | ............. C08L 89/00 |
| WO | 2011002730 A1 | 1/2011 | |
| WO | 2011/138458 A1 | 11/2011 | |
| WO | 2012/166414 A1 | 12/2012 | |
| WO | 2016/102444 A1 | 6/2016 | |

OTHER PUBLICATIONS

Sartuqui, Javier; Biomimetic fiber mesh scaffolds based on gelatin and hydroxyapatite nano-rods: Designing Intrinsic skills to attain bone reparation abilities; J. Sartuqui et al./ Colloids and Surfaces B: Bioi11te1faces 145 (2016) 382-391.

XP009194898; Broderick, Emmett; Enzymatic Stabilization of Gelatin-Based Scaffolds; Received Dec. 9, 2003; revised Feb. 3, 2004; accepted May 3, 2004; Published online Oct. 15, 2004 in Wiley InterScience (www.interscience.wiley.com).

Plashchina, Irina; Phase behavior of gelatin in the presence of pectin in water-acid medium; Received: Jun. 29, 2006 / Revised version: Oct. 3, 2006 / Accepted: Oct. 4, 2006 Published online: Oct. 13, 2006 -Â@ Springer-Verlag 2006.

Bae, Ho; Effects of transglutaminase-induced cross-linking on properties of fish gelatin-nanoclay composite film; Food Chemistry 114 (2009) 180-189.

Zitko, V; Reaction-Pectin With Gold (II) Composition—Complexes · Pectine and .Gel; HTTPS://translate.googleusercontent.com/translate.

Perez-Mateos et al. (Food Hydrocolloids 23, 2009, 53-61)(Year:2009).

AAK Handbook Vegetable Oils and Fats, 2007, AAK, Denmark, second ed, p. 1.

* cited by examiner

FIRE-PROTECTING INSULATION PRODUCT AND USE OF SUCH PRODUCT

REFERENCE TO RELATED APPLICATIONS

This application is a U.S. national stage application of PCT/EP2017/079090, filed. Nov. 13, 2017, which claims priority to PCT/EP2017/061418 and PCT/EP2017/061419, both filed May 11, 2017. The entire content of each application is incorporated herein by reference.

FIELD OF THE INVENTION

The present invention relates to a fire-protecting insulation product comprising mineral wool fibres.

BACKGROUND OF THE INVENTION

Mineral wool fibrous products are known to have fire-protecting properties. Examples are known from EP 1 086 055, EP 1 928 796, WO 97/20780 or EP 3 187 474 A1.

Conventionally, phenol-formaldehyde resins which can be economically produced have been used as binder compositions for bonding together mineral wool fibres.

However, these binders suffer from the disadvantage that they contain formaldehyde and they are therefore potentially harmful and there is a desire to replace these conventional binders with formaldehyde-free binders.

Non-phenol-formaldehyde binders are often sugar based binders, such as for example the compositions disclosed in EP2990494A1, PCT/EP2015/080758, WO2007/014236, WO2011/138458 and WO2009/080938.

However, all these binders suffer from the disadvantage that they require high temperatures for curing which makes it necessary to apply heat over a prolonged time to cure the binder and bond the mineral fibres to each other. Accordingly, in the production, the binder must be cured after the product has been formed. This curing is achieved by heating the product in an oven, typically to a temperature of 200-250° C. for a certain amount of time. This heating adds to the production time and the production costs just as it sets some constrains in which materials can be added to the product since the materials must be capable of withstanding this elevated heating. Further, the high temperature curing of these known binders causes emissions of harmful or irritating substances which must be handled.

Accordingly, it is an object of the present invention to provide a fire-protection insulating product which reduces or eliminates the above-mentioned drawbacks.

SUMMARY OF THE INVENTION

These objects are achieved a fire-protecting insulation, product comprising air-laid mineral wool fibres and a binder, said binder being the result of curing a binder composition comprising at least one hydrocolloid, and said product further comprising a particulate endothermic material.

It is surprisingly found that it is possible to use a binder which can be cured at relatively low temperatures which allows further substances to be added to the mineral wool fire-protecting product in order to further improve the fire-protecting properties of the product.

Furthermore, since the binder used in the product in some embodiments does usually not contain any harmful substances and does usually not set free any harmful substances during the curing a more environmentally friendly production can be achieved.

Preferably, the binder further comprises at least one fatty acid ester of glycerol.

In one embodiment the particulate endothermic material is distributed evenly within the fire-protecting insulation product.

However, in a preferred embodiment the product has a first and a second face section with a core section therebetween and the particulate endothermic material is distributed such that there is a higher concentration of endothermic material in the core section of the mineral fibre wool product than in the face sections. This is advantageous as the endothermic material absorbs energy and thereby delays the heat from a fire in spreading from one side to the other in a mineral wool product according to the invention. By having the particulate material mainly in the core section the risk that it falls out of the product during handling is minimised. Furthermore, it is advantageous, since such product provides equally good fire protection from either side thereof.

In an embodiment of the invention the endothermic material is selected from the group consisting of gypsum, magnesium hydroxide, hydromagnesite, aluminium hydroxide and aluminium trihydroxide.

In a second aspect of the invention there is provided a use of a fire-protecting insulation product comprising air-laid mineral wool fibres and a binder, said binder being the result of curing a binder composition comprising at least one hydrocolloid, and said product comprising a particulate endothermic material.

Accordingly, the product according to the invention may be used for fire-protection of a structure, such as a building structure, as an insert for a fire door or for fire-protection of a ventilation duct.

BRIEF DESCRIPTION OF THE DRAWINGS

The disclosure is explained with reference to the accompanying drawings, in which.

DETAILED DESCRIPTION OF THE INVENTION

The Mineral Wool Element

Figure 1:
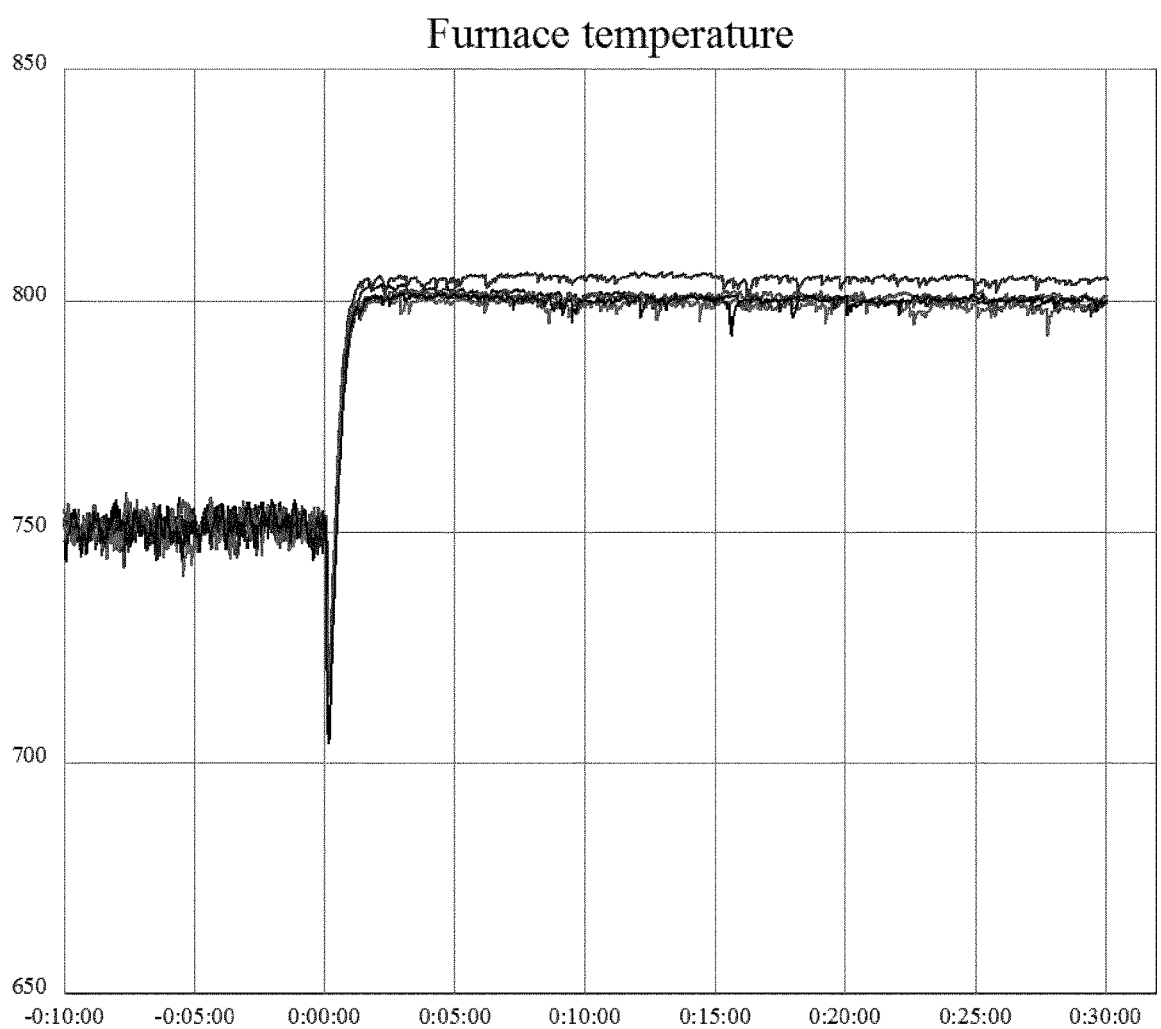
FIG. 1 shows a graph for the product according to the present invention (without endothermic material)

Mineral wool elements generally comprise man-made vitreous fibres (MMVF) such as, e.g., glass fibres, ceramic fibres, basalt fibres, slag wool, mineral wool and stone wool, which are bonded together by a cured mineral wool binder which conventionally is a thermoset polymeric binder material. For use as thermal or acoustical insulation products, bonded mineral fibre mats are generally produced by converting a melt made of suitable raw materials to fibres in conventional manner, for instance by a spinning cup process or by a cascade rotor process. The fibres are blown into a forming chamber and, while airborne and while still hot, are sprayed with a binder solution and randomly deposited as a mat or web onto a travelling conveyor. The fibre web is then transferred to a curing oven where heated air is blown through the web to cure the binder and rigidly bond the mineral fibres together.

If desired, the web may be subjected to a shaping process before curing. The bonded mineral fibre element may be cut to a desired format e.g., in the form of a batt. Thus, the mineral wool elements, for instance, have the form of woven and nonwoven fabrics, mats, batts, slabs, sheets, plates, strips, rolls, granulates and other shaped articles which find use for example, as thermal or acoustical insulation materials, vibration damping, construction materials, facade insulation, reinforcing materials for roofing or flooring applications, as filter stock, as horticultural growing media and in other applications. Mineral wool elements are also known to have excellent fire resisting properties and are therefore often used for fire protecting of structures, such as building structures, technical installations or as inserts in fire doors.

The Mineral Wool Binder

The binder in the present invention results from curing a binder composition which comprises at least one hydrocolloid. In a preferred embodiment the binder composition also comprises at least one fatty acid ester of glycerol.

In a preferred embodiment, the binders used in the present invention are formaldehyde free.

For the purpose of the present application, the term "formaldehyde free" is defined to characterize a mineral wool product where the emission is below 5 µg/m$^2$/h of formaldehyde from the mineral wool product, preferably below 3 µg/m$^2$/h. Preferably, the test is carried out in accordance with ISO 16000 for testing aldehyde emissions.

A surprising advantage of embodiments of mineral wool products according to the present invention is that they show self-healing properties. After being exposed to very harsh conditions when mineral wool products loose a part of their strength, the mineral wool products according to the present invention can regain a part of, the whole of or even exceed the original strength. In one embodiment, the aged strength is at least 80%, such as at least 90%, such as at least 100%, such as at least 130%, such as at least 150% of the unaged strength. This is in contrast to conventional mineral wool products for which the loss of strength after being exposed to harsh environmental conditions is, irreversible. While not wanting to be bound to any particular theory, the present inventors believe that this surprising property in mineral wool products according to the present invention is due to the complex nature of the bonds formed in the network of the cured binder composition, such as the protein crosslinked by the phenol and/or quinone containing compound or crosslinked by an enzyme, which also includes quaternary structures and hydrogen bonds and allows bonds in the network to be established after returning to normal environmental conditions. For an insulation product, which when e.g. used as thermal insulation and fire protection of technical installations which occasionally may operate at high temperatures, this is an important advantage for the long term stability of the product.

Hydrocolloid

Hydrocolloids are hydrophilic polymers, of vegetable, animal, microbial or synthetic origin, that generally contain many hydroxyl groups and may be polyelectrolytes. They are widely used to control the functional properties of aqueous foodstuffs.

Hydrocolloids may be proteins or polysaccharides and are fully or partially soluble in water and are used principally to increase the viscosity of the continuous phase (aqueous phase) i.e. as gelling agent or thickener. They can also be used as emulsifiers since their stabilizing effect on emulsions derives from an increase in viscosity of the aqueous phase.

A hydrocolloid usually consists of mixtures of similar, but not identical molecules and arising from different sources and methods of preparation. The thermal processing and for example, salt content, pH and temperature all affect the physical properties they exhibit. Descriptions of hydrocolloids often present idealised structures but since they are natural products (or derivatives) with structures determined by for example stochastic enzymatic action, not laid down exactly by the genetic code, the structure may vary from the idealised structure.

Many hydrocolloids are polyelectrolytes (for example alginate, gelatin, carboxymethylcellulose and xanthan gum).

Polyelectrolytes are polymers where a significant number of the repeating units bear an electrolyte group. Polycations and polyanions are polyelectrolytes. These groups dissociate in aqueous solutions (water), making the polymers charged. Polyelectrolyte properties are thus similar to both electrolytes (salts) and polymers (high molecular weight compounds) and are sometimes called polysalts.

The charged groups ensure strong hydration, particularly on a per-molecule basis. The presence of counterions and co-ions (ions with the same charge as the polyelectrolyte) introduce complex behavior that is ion-specific.

A proportion of the counterions remain tightly associated with the polyelectrolyte, being trapped in its electrostatic field and so reducing their activity and mobility.

In one embodiment the binder composition comprise one or more) counter-ion(s) selected from the group of Mg2+, Ca2+, Sr2+, Ba2+.

Another property of a polyelectrolyte is the high linear charge density (number of charged groups per unit, length).

Generally neutral hydrocolloids are less soluble whereas polyelectrolytes are more soluble.

Many hydrocolloids also gel. Gels are liquid-water-containing networks showing solid-like behavior with characteristic strength, dependent on their concentration, and hardness and brittleness dependent on the structure of the hydrocolloid(s) present.

Hydrogels are hydrophilic crosslinked polymers that are capable of swelling to absorb and hold vast amounts of water. They are particularly known from their use in sanitary products. Commonly used materials make use of polyacrylates, but hydrogels may be made by crosslinking soluble hydrocolloids to make an insoluble but elastic and hydrophilic polymer.

Examples of hydrocolloids comprise: Agar agar, Alginate, Arabinoxylan, Carrageenan, Carboxymethylcellulose, Cellulose, Curdlan, Gelatin, Gellert, β-Glucan, Guar gum, Gum arabic, Locust bean gum, Pectin, Starch, Xanthan gum. In one embodiment, the at least one hydrocolloid is selected from the group consisting of gelatin, pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

Examples of polyelectrolytic hydrocolloids comprise: gelatin, pectin, alginate, carrageenan, gum arabic, xanthan gum, cellulose derivatives such as carboxymethylcellulose.

In one embodiment, the at east one hydrocolloid is a polyelectrolytic hydrocolloid.

In one embodiment, the at least one hydrocolloid is selected from the group consisting of gelatin, pectin, alginate, carrageenan, gum arabic, xanthan gum, cellulose derivatives such as carboxymethylcellulose.

In one embodiment, the at least one hydrocolloid is a gel former.

In one embodiment, the at least one hydrocolloid is used in form of a salt, such as a salt of Na+, K+, NH4+, Mg2+, Ca2+, Sr2+, Ba2+.

Gelatin

Gelatin is derived from chemical degradation of collagen. Gelatin may also be produced by recombinant techniques.

Gelatin is water soluble and has a molecular weight of 10,000 to 500,000 g/mol, such as 30,000 to 300,000 g/mol dependent on the grade of hydrolysis. Gelatin is a widely used food product and it is therefore generally accepted that this compound is totally non-toxic and therefore no precautions are to be taken when handling gelatin.

Gelatin is a heterogeneous mixture of single or multi-stranded polypeptides, typically showing helix structures. Specifically, the triple helix of type I collagen extracted from skin and bones, as a source for gelatin, is composed of two $\alpha 1(I)$ and one $\alpha 2(I)$ chains.

Gelatin solutions may undergo coil-helix transitions.

A type gelatins are produced by acidic treatment. B type gelatins are produced by basic treatment.

Chemical cross-links may be introduced to gelatin. In one embodiment, transglutaminase is used to link lysine to glutamine residues; in one embodiment, glutaraldehyde is used to link lysine to lysine, in one embodiment, tannins are used to link lysine residues.

The gelatin can also be further hydrolysed to smaller fragments of down to 3000 g/mol.

On cooling a gelatin solution, collagen like helices may be formed.

Other hydrocolloids may also comprise helix structures such as collagen like helices. Gelatin may form helix structures.

In one embodiment, the cured binder comprising hydrocolloid comprises helix structures.

In one embodiment, the at least one hydrocolloid is a low strength gelatin, such as a gelatin having a gel strength of 30 to 125 Bloom.

In one embodiment, the at least one hydrocolloid is a medium strength gelatin, such as a gelatin having a gel strength of 125 to 180 Bloom.

In one embodiment, the at least one hydrocolloid is a high strength gelatin, such as a gelatin having a gel strength of 180 to 300 Bloom.

In a preferred embodiment, the gelatin is preferably originating from one or more sources from the group consisting of mammal, bird species, such as from cow, pig, horse, fowl, and/or from scales, skin of fish.

In one embodiment, urea may be added to the binder compositions used in the present invention. The inventors have found that the addition of even small amounts of urea causes denaturation of the gelatin, which can slow down the gelling, which might be desired in some embodiments. The addition of urea might also lead to a softening of the product.

The inventors have found that the carboxylic acid groups in gelatins interact strongly with trivalent and tetravalent ions, for example aluminum salts. This is especially true for type B gelatins which contain more carboxylic acid groups than type A gelatins.

The present inventors have found that in some embodiments, curing/drying of binder compositions used in the present invention including gelatin should not start off at very high temperatures.

The inventors have found that starting the curing at low temperatures may lead to stronger products. Without being bound to any particular theory, it is assumed by the inventors that starting curing at high temperatures may lead to an impenetrable outer shell of the binder composition which hinders water from underneath to get out.

Surprisingly, the binders used in the present invention including gelatins are very heat resistant. The present inventors have found that in some embodiments the cured binders can sustain temperatures up to 300° C. without degradation.

Pectin

Pectin is a heterogeneous grouping of acidic structural polysaccharides, found in fruit and vegetables which form acid-stable gels.

Generally, pectins do not possess exact structures, instead it may contain up to 17 different monosaccharides and over 20 types of different linkages.

D-galacturonic acid residues form most of the molecules.

Gel strength increases with increasing Ca2+ concentration but reduces with temperature and acidity increase (pH<3).

Pectin may form helix structures.

The gelling ability of the di-cations is similar to that found with alginates (Mg2+ is much less than for Ca2+, Sr2+ being less than for Ba2+).

Alginate

Alginates are scaffolding polysaccharides produced by brown seaweeds.

Alginates are linear unbranched polymers containing $\beta$-(1,4)-linked D-mannuronic acid (M) and $\alpha$-(1,4)-linked L-guluronic acid (G) residues. Alginate may also be a bacterial alginate, such as which are additionally 0-acetylated. Alginates are not random copolymers but, according to the source algae, consist of blocks of similar and strictly alternating residues (that is, MMMMMM, GGGGGG and GMGMGMGM), each of which have different conformational preferences and behavior. Alginates may be prepared with a wide range of average molecular weights (50-100000 residues). The free carboxylic acids have a water molecule H30+ firmly hydrogen bound to carboxylate. Ca2+ ions can replace this hydrogen bonding, zipping guluronate, but not mannuronate, chains together stoichiometrically in a so-called egg-box like conformation. Recombinant epimerases with different specificities may be used to produce designer alginates.

Alginate may form helix structures.

Carrageenan

Carrageenan is a collective term for scaffolding polysaccharides prepared by alkaline extraction (and modification) from red seaweed.

Carrageenans are linear polymers of about 25,000 galactose derivatives with regular but imprecise structures, dependent on the source and extraction conditions.

κ-carrageenan (kappa-carrageenan) is produced by alkaline elimination from μ-carrageenan isolated mostly from the tropical seaweed Kappaphycus alvarezii (also known as Eucheuma cottonii).

ι-carrageenan (iota-carrageenan) is produced by alkaline elimination from v-carrageenan isolated mostly from the Philippines seaweed Eucheuma denticulatum (also called Spinosum).

λ-carrageenan (lambda-carrageenan) (isolated mainly from Gigartina pistillata or Chondrus crispus) is converted into θ-carrageenan (theta-carrageenan) by alkaline elimination, but at a much slower rate than causes the production of ι-carrageenan and κ-carrageenan.

The strongest gels of κ-carrageenan are formed with K+ rather than Li+, Na+, Mg2+, Ca2+, or Sr2+.

All carrageenans may form helix structures.

Gum Arabic

Gum arabic is a complex and variable mixture of arabinogalactan oligosaccharides, polysaccharides and glycoproteins. Gum arabic consists of a mixture of lower relative molecular mass polysaccharide and higher molecular weight hydroxyproline-rich glycoprotein with a wide variability.

Gum arabic has a simultaneous presence of hydrophilic carbohydrate and hydrophobic protein.

Xanthan Gum

Xanthan gum is a microbial desiccation-resistant polymer prepared e.g. by aerobic submerged fermentation from Xanthomonas campestris.

Xanthan gum is an anionic polyelectrolyte with a β-(1,4)-D-glucopyranose glucan (as cellulose) backbone with side chains of -(3,1)-α-linked D-mannopyranose-(2,1)-β-D-glucuronic acid-(4,1)-β-D-mannopyranose on alternating residues.

Xanthan gums natural state has been proposed to be bimolecular antiparallel double helices. A conversion between the ordered double helical conformation and the single more-flexible extended chain may take place at between 40° C.-80° C. Xanthan gums may form helix structures.

Xanthan gums may contain cellulose.

Cellulose Derivatives

An example of a cellulose derivative, is carboxymethylcellulose.

Carboxymethylcellulose (CMC) is a chemically modified derivative of cellulose formed by its reaction with alkali and chloroacetic acid.

The CMC structure is based on the β-(1,4)-D-glucopyranose polymer of cellulose. Different preparations may have different degrees of substitution, but it is generally in the range 0.6-0.95 derivatives per monomer unit Agar Agar Agar agar is a scaffolding polysaccharide prepared from the same family of red seaweeds (Rhodophycae) as the carrageenans. It is commercially obtained from species of Gelidium and Graciariae.

Agar agar consists of a mixture of agarose and agaropectin. Agarose is a linear polymer, of relative molecular mass (molecular weight) about 120,000, based on the -(1,3)-β-D-galactopyranose-(1,4)-3,6-anhydro-α-L-galactopyranose unit.

Agaropectin is a heterogeneous mixture of smaller molecules that occur in lesser amounts.

Agar agar may form helix structures.

Arabinoxylan

Arabinoxylans are naturally found in the bran of grasses (Graminiae).

Arabinoxylans consist of α-L-arabinofuranose residues attached as branch-points to β-(1,4)-linked D-xylopyranose polymeric backbone chains.

Arabinoxylan may form helix structures.

Cellulose

Cellulose is a scaffolding polysaccharide found in, plants as microfibrils (2-20 nm diameter and 100-40 000 nm long). Cellulose is mostly prepared from wood pulp. Cellulose is also produced in a highly hydrated form by some bacteria (for example, *Acetobacter xylinum*).

Cellulose is a linear polymer of β-(1,4)-D-glucopyranose units in 4C1 conformation. There are four crystalline forms, Iα, Iβ, II and III.

Cellulose derivatives may be methyl cellulose, hydroxypropyl methylcellulose, hydroxyethyl methylcellulose, hydroxyethyl cellulose, hydroxypropyl cellulose.

Curdlan

Curdlan is a polymer prepared commercially from a mutant strain of Alcaligenes faecalis var, myxogenes. Curdan (curdlan gum) is a moderate relative molecular mass, unbranched linear 1,3 β-D glucan with no side-chains.

Curdlan may form helix structures.

Curdlan gum is insoluble in cold water but aqueous suspensions plasticize and briefly dissolve before producing reversible gels on heating to around 55° C., Heating at higher temperatures produces more resilient irreversible gels, which then remain on cooling.

Scleroglucan is also a 1,3 β-D glucan but has additional 1,6 β-links that confer solubility under ambient conditions.

Gellan

Gellan gum is a linear tetrasaccharide 4)-L-rharrmopyranosyl-(α-1,3)-D-glucopyranosyl-(β-1,4)-D-glucuronopyranosyl-(β-1,4)-D-glucopyranosyl-(β-1, with O(2) L-glyceryl and O(6) acetyl substituents on the 3-linked glucose.

Gellan may form helix structures.

β-Glucan

β-Glucans occur n the bran of grasses (Gramineae).

β-Glucans consist of linear unbranched polysaccharides of linked β-(1,3)- and β-(1,4)-D-glucopyranose units in a non-repeating but non-random order.

Guar Gum

Guar gum (also called guaran) is a reserve polysaccharide (seed flour) extracted from the seed of the leguminous shrub Cyamopsis tetragonoloba.

Guar gum is a galactomannana similar to locust bean gum consisting of a (1,4)-linked β-D-mannopyranose backbone with branch points from their 6-positions linked to α-D-galactose (that is, 1,6-linked-α-D-galactopyranose).

Guar gum is made up of non-ionic polydisperse rod-shaped polymer.

Unlike locust bean gum, it does not form gels.

Locust Bean Gum

Locust bean gum (also called Carob bean gum and Carubin) is a reserve polysaccharide (seed flour) extracted from the seed (kernels) of the carob tree (Ceratonia siliqua).

Locust bean gum is a galactomannana similar to guar gum consisting of a (1,4)-linked β-D-mannopyranose backbone with branch points from their 6-positions linked to α-D-galactose (that is, 1,6-linked α-D-galactopyranose).

Locust bean gum is polydisperse consisting of non-ionic molecules.

Starch

Starch consists of two types of molecules, amylose (normally 20-30%) and amylopectin (normally 70-80%). Both consist of polymers of α-D-glucose units in the 4C1 conformation. In amylose these are linked -(1,4)-, with the ring oxygen atoms all on the same side, whereas in amylopectin about one residue in every twenty or so is also linked -(1,6)-forming branch-points. The relative proportions of amylose to amylopectin and -(1,6)-branch-points both depend on the source of the starch. The starch may derive from the source of corn (maize), wheat, potato, tapioca and rice. Amylopectin (without amylose) can be isolated from 'waxy' maize starch whereas amylose (without amylopectin) is best isolated after specifically hydrolyzing, the amylopectin with pullulanase.

Amylose may form helix structures.

In one embodiment, the at least one hydrocolloid is a functional derivative of starch such as cross-linked, oxidized, acetylated, hydroxypropylated and partially hydrolyzed starch.

In a preferred embodiment, the binder composition comprises at least two hydrocolloids, wherein one hydrocolloid is gelatin and the at least one other hydrocolloid is selected from the group consisting of pectin, starch, alginate, agar agar, carrageenan, gellan gum, guar gum, gum arabic, locust bean gum, xanthan gum, cellulose derivatives such as carboxymethylcellulose, arabinoxylan, cellulose, curdlan, β-glucan.

In one embodiment, the binder composition comprises at least two hydrocolloids, wherein one hydrocolloid is gelatin and the at least other hydrocolloid is pectin.

In one embodiment, the binder composition comprises at least two hydrocolloids, wherein one hydrocolloid is gelatin and the at least other hydrocolloid is alginate.

In one embodiment, the binder composition comprises at least two hydrocolloids, wherein one hydrocolloid is gelatin and the at least other hydrocolloid is carboxymethylcellulose.

In a preferred embodiment, the binder composition used in the present invention comprises at least two hydrocolloids, wherein one hydrocolloid is gelatin and wherein the gelatin is present in the aqueous binder composition in an amount of 10 to 95 wt.-%, such as 20 to 80 wt-%, such as 30 to 70 wt.-%, such as 40 to 60 wt.-%, based on the weight of the hydrocolloids.

In one embodiment, the binder composition comprises at least two hydrocolloids, wherein the one hydrocolloid and the at least other hydrocolloid have complementary charges.

In one embodiment, the one hydrocolloid is one or more of gelatin or gum arabic having complementary charges from one or more hydrocolloid(s) selected from the group of pectin, alginate, carrageenan, xanthan gum or carboxymethylcellulose.

In one embodiment, the binder composition is capable of curing at a temperature of not more than 95° C., such as 5-95° C., such as 10-80° C., such as 20-60° C., such as 40-50° C.

In one embodiment, the aqueous binder composition used in the present invention is not a thermoset binder.

A thermosetting composition is in a soft solid or viscous liquid state, preferably comprising a prepolymer, preferably comprising a resin, that changes irreversibly into an infusible, insoluble polymer network by curing. Curing is typically induced by the action of heat, whereby typically temperatures above 95° C. are needed.

A cured thermosetting resin is called a thermoset or a thermosetting plastic/polymer—when used as the bulk material in a polymer composite, they are referred to as the thermoset polymer matrix. In one embodiment, the aqueous, binder composition used in the present invention does not contain a poly(meth)acrylic acid, a salt of a poly(meth)acrylic acid or an ester of a poly(meth)acrylic acid.

In one embodiment, the at least one hydrocolloid is a biopolymer or modified biopolymer.

Biopolymers are polymers produced by living organisms. Biopolymers may contain monomeric units that are covalently bonded to form larger structures.

There are three main classes of biopolymers, classified according to the monomeric units used and the structure of the biopolymer formed: Polynucleotides (RNA and DNA), which are long polymers composed of 13 or more nucleotide monomers; Polypeptides, such as proteins, which are polymers of amino acids; Polysaccharides, such as linearly bonded polymeric carbohydrate structures.

Polysaccharides may be linear or branched; they are typically joined with glycosidic bonds. In addition, many saccharide units can undergo various chemical modifications, and may form parts of other molecules, such as glycoproteins.

In one embodiment, the at least one hydrocolloid is a biopolymer or modified biopolymer with a polydispersity index regarding molecular mass distribution of 1, such as 0.9 to 1.

In one embodiment, the binder composition comprises proteins from animal sources, including collagen, gelatin, and hydrolysed gelatin, and the binder composition further comprises at least one phenol and/or quinone containing compound, such as tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the binder composition comprises proteins from animal sources, including collagen, gelatin, and hydrolysed gelatin, and wherein the binder composition further comprises at least one enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

Fatty Acid Ester of Glycerol

In a preferred embodiment the binder composition also comprises a component in form of at least one fatty acid ester of glycerol.

A fatty acid is a carboxylic acid with an aliphatic chain, which is either saturated or unsaturated.

Glycerol is a polyol compound having the IUPAC name propane-1,2,3-triol.

Naturally occurring fats and oils are glycerol esters with fatty acids (also called triglycerides).

For the purpose of the present invention, the term fatty acid ester of glycerol refers to mono-, di-, and tri-esters of glycerol with fatty acids.

While the term fatty acid can in the context of the present invention be any carboxylic acid with an aliphatic chain, it is preferred that it is carboxylic acid with an aliphatic chain having 4 to 28 carbon atoms, preferably of an even number of carbon atoms. Preferably, the aliphatic chain of the fatty acid is unbranched.

In a preferred embodiment, the at least one fatty acid ester of glycerol is in form of a plant oil and/or animal oil. In the context of the present invention, the term "oil" comprises at least one fatty acid ester of glycerol in form of oils or fats.

In one preferred embodiment, the at least one fatty acid ester of glycerol is a plant-based oil.

In a preferred embodiment, the at least one fatty acid ester of glycerol is in form of fruit pulp fats such as palm oil, olive oil, avocado oil; seed-kernel fats such as lauric acid oils, such as coconut oil, palm kernel oil, babassu oil and other palm seed oils, other sources of lauric acid oils; palmitic-stearic acid oils such as cocoa butter, rhea butter, borneo tallow and related fats (vegetable butters); palmitic acid oils such as cottonseed oil, kapok and related oils, pumpkin seed oil, corn (maize) oil, cereal oils; oleic-linoleic acid oils such as sunflower oil, sesame oil, linseed oil, perilla oil, hempseed oil, teaseed oil, safflower and niger seed oils, grapeseed oil, poppyseed oil, leguminous oil such as soybean oil, peanut oil, lupine oil; cruciferous oils such as rapeseed oil, mustard seed oil; conjugated acid oils such as tung oil and related oils, oiticica oil and related oils; substituted fatty acid oils such as castor oil, chaulmoogra, hydnocarpus and gorli oils, vernonia oil; animal fats such as land-animal fats such as lard, beef tallow, mutton tallow, horse fat, goose fat, chicken fat; marine oils such as whale oil and fish oil.

In a preferred embodiment, the at least one fatty acid ester of glycerol is in form of a plant oil, in particular selected from one or more components from the group consisting of linseed oil, olive oil, tung oil, coconut oil, hemp oil, rapeseed oil, and sunflower oil.

In a preferred embodiment, the at least one fatty acid ester of glycerol is selected from one or more components from the group consisting of a plant oil having an iodine number in the range of approximately 136 to 178, such as a linseed oil having an iodine number in the range of approximately 136 to 178, a plant oil having an iodine number in the range of approximately 80 to 88, such as an olive oil, having an iodine number in the range of approximately 80 to 88, a plant oil having an iodine number in the range of approximately 163 to 173, such as tong oil having an iodine number in the range of approximately 163 to 173, a plant oil having an iodine number in the range of approximately 7 to 10, such as coconut oil having an iodine number in the range of approximately 7 to 10, a plant oil having an iodine number in the range of approximately 140 to 170, such as hemp oil having an iodine number in the range of approximately 140 to 170, a plant oil having an iodine number in the range of approximately 94 to 120, such as a rapeseed oil having an iodine number in the range of approximately 94 to 120, a plant oil having an iodine number in the range of approximately 118 to 144, such as a sunflower oil having an iodine number in the range of approximately 118 to 144.

In one embodiment, the at least one fatty acid ester of glycerol is not of natural origin.

In one embodiment, the at least one fatty acid ester of glycerol is a modified plant or animal oil.

In one embodiment, the at least one fatty acid ester of glycerol comprises at least one trans-fatty acid.

In an alternative preferred embodiment, the at least one fatty acid ester of glycerol is in form of an animal oil, such as a fish oil.

The present inventors have found that an important parameter for the fatty acid ester of glycerol used in the binders in the present invention is the amount of unsaturation in the fatty acid. The amount of unsaturation in fatty acids is usually measured by the iodine number (also called iodine value or iodine absorption value or iodine index). The higher the iodine number, the more C=C bonds are present in the fatty acid. For the determination of the iodine number as a measure of the unsaturation of fatty acids, we make reference to Thomas, Alfred (2002) "Fats and fatty oils" in Ullmann's Encyclopedia of industrial chemistry, Weinheim, Wiley-VCH.

In a preferred embodiment, the at least one fatty acid ester of glycerol comprises a plant oil and/or animal oil having a iodine number of ≥75, such as 75 to 180, such as ≥130, such as 130 to 180.

In an alternative preferred embodiment, the at least one fatty acid ester of glycerol comprises a plant oil and/or animal oil having a iodine number of ≤100, such as ≤25.

In one embodiment, the at least one fatty acid ester of glycerol is a drying oil. For a definition of a drying oil, see both, Ulrich (2012) "Drying oils and related products" in Ullmann's Encyclopedia of industrial chemistry, Weinheim, Wiley-VCH.

Accordingly, the present inventors have found that particularly good results are achieved when the iodine number is either in a fairly high range or, alternatively, in a fairly flow range. While not wanting to be bound by any particular theory, the present inventors assume that the advantageous properties inflicted by the fatty acid esters of high iodine number on the one hand and low iodine number on the other hand are based on different mechanisms. The present inventors assume that the advantageous properties of glycerol esters of fatty acids having a high iodine number might be due to the participation of the C=C double-bonds found in high numbers in these fatty acids in a crosslinking reaction, while the glycerol esters of fatty acids having a low iodine number and lacking high amounts of C=C double-bonds might allow a stabilization of the cured binder by van der Waals interactions.

In a preferred embodiment, the content of the fatty acid ester of glycerol is 0.5 to 40, such as 1 to 30, such as 1.5 to 20, such as 3 to 10, such as 4 to 75 wt.-%, based on dry hydrocolloid basis.

In one embodiment, the binder composition comprises gelatin, and the binder composition further comprises a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups, preferably tannic acid, and the binder composition further comprises at least one fatty acid ester of glycerol, such as at least one fatty acid ester of glycerol selected from one or more components from the group consisting of linseed oil, olive oil, tung oil, coconut oil, hemp oil, rapeseed oil, and sunflower oil.

In one embodiment, the binder composition comprises gelatin, and the binder composition further comprises at least one enzyme which is a transglutaminase (EC 2.3.2.13), and the binder composition further comprises at least one fatty acid ester of glycerol, such as at least one fatty acid ester of glycerol selected from one or more components from the group consisting of linseed oil, olive oil, tung oil, coconut oil, hemp oil, rapeseed oil, and sunflower oil.

In one embodiment, the aqueous binder composition is formaldehyde-free.

In one embodiment, the binder composition is consisting essentially of:
 at least one hydrocolloid;
 at least one fatty acid ester of glycerol;
 optionally at least one pH-adjuster;
 optionally at least one crosslinker;
 optionally at least one anti-fouling agent;
 optionally at least one anti-swelling agent;
 water.

In one embodiment, an oil may be added to the binder composition.

In one embodiment, the at least one oil is a non-emulsified hydrocarbon oil.

In one embodiment, the at least one oil is an emulsified hydrocarbon oil.

In one embodiment, the at least one oil is a plant-based oil.

In one embodiment, the at least one crosslinker is tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, the at least one crosslinker is an enzyme selected from the group consisting of transglutaminase (EC 2.3.2.13), protein disulfide isomerase (EC 5.3.4.1), thiol oxidase (EC 1.8.3.2), polyphenol oxidase (EC 1.14.18.1), in particular catechol oxidase, tyrosine oxidase, and phenoloxidase, lysyl oxidase (EC 1.4.3.13), and peroxidase (EC 1.11.1.7).

In one embodiment, the at least one anti-swelling agent is tannic acid and/or tannins.

In one embodiment, the at least one anti-fouling agent s an antimicrobial agent.

Antimicrobial agents may be benzoic acid, propionic acid, sodium benzoate, sorbic acid, and potassium sorbate to inhibit the outgrowth of both bacterial and fungal cells. However, natural biopreservatives may, be used. Chitosan is regarded as being antifungal and antibacterial. The most frequently used biopreservatives for antimicrobial are lysozyme and nisin. Common other biopreservatives that may be used are bacteriocins, such as lacticin and pediocin and antimicrobial enzymes, such as chitinase and glucose oxidase. Also, the use of the enzyme lactoperoxidase (LPS) presents antifungal and antiviral activities. Nature antimicrobial agents may also be used, such as tannins, rosemary, and garlic essential oils, oregano, lemon grass, or cinnamon oil at different concentrations.

Mineral Fibre Product

In the fire-protecting insulation product according to the present invention the mineral fibres are bound by a binder as described above.

In one embodiment, the loss on ignition (LOI) of the mineral wool product according to the present invention is within the range of 0.1 to 25.0%, such as 0.3 to 18.0%, such as 0.5 to 12.0%, such as 0.7 to 8.0% by weight.

In one embodiment, the binder is not crosslinked.

In an alternative embodiment, the binder is crosslinked.

Reaction of the Binder Components

The present inventors have found that in some embodiments of the mineral wool product according to the present invention are best to be produced when the binder is applied to the mineral fibres under acidic conditions. Therefore, in a preferred embodiment, the binder applied to the mineral fibres comprises a pH-adjuster, in particular in form of a pH buffer.

In a preferred embodiment, the binder in its uncured state has a pH value of less than 8, such as less than 7, such as less than 6.

The present inventors have found that in some embodiments, the curing of the binder is strongly accelerated under alkaline conditions. Therefore, in one embodiment, the binder composition for mineral fibres comprises a pH-adjuster, preferably in form of a base, such as organic base, such as amine or salts thereof, inorganic bases, such as metal hydroxide, such as KOH or NaOH, ammonia or salts thereof.

In a particular preferred embodiment, the pH adjuster is an alkaline metal hydroxide, in particular NaOH.

In a preferred embodiment, the binder composition used in the present invention has a pH of 7 to 10, such as 7.5 to 9.5, such as 8 to 9.

Other additives may be components such as one or more reactive or nonreactive silicones and may be added to the binder. Preferably, the one or more reactive or nonreactive silicone is selected from the group consisting of silicone constituted of a main chain composed of organosiloxane residues, especially diphenylsiloxane residues, alkylsiloxane residues, preferably dimethylsiloxane residues, bearing at least one hydroxyl, acyl, carboxyl or anhydride, amine, epoxy or vinyl functional group capable of reacting with at least one of the constituents of the binder composition and is preferably present in an amount of 0.1-15 weight-%, preferably from 0.1-10 weight-%, more preferably 0.3-8 weight-%, based on the total binder mass.

In one embodiment, an anti-fouling agent, may be added to the binder.

In a preferred embodiment, the anti-fouling agent is a tannin, in particular a tannin selected from one or more components from the group consisting of tannic acid, condensed tannins (proanthocyanidins), hydrolysable tannins, gallotannins, ellagitannins, complex tannins, and/or tannin originating from one or more of oak, chestnut, staghorn sumac and fringe cups.

In one embodiment, an anti-swelling agent may be added to the binder, such as tannic acid and/or tannins.

Further additives may be additives containing calcium ions and antioxidants.

In one embodiment, the binder composition used in the present invention contains additives in form of linkers containing acyl groups and/or amine groups and/or thiol groups. These linkers can strengthen and/or modify the network of the cured binder.

In one embodiment, the binder compositions used in the present invention contain further additives in form of additives selected from the group consisting of PEG-type reagents, silanes, and hydroxylapatites.

Properties of the Mineral Wool Product

In a preferred embodiment, the density of the mineral wool fire-protecting product is in the range of 10-1200 kg/m$^3$, such as 30-800 kg/m$^3$, such as 40-600 kg/m$^3$, such as 50-250 kg/m$^3$, such as 60-200 kg/m$^3$.

Fiber Forming Apparatus

There are various types of centrifugal spinners for fiberising mineral melts.

A conventional centrifugal spinner is a cascade spinner which comprises a sequence of a top (or first) rotor and a subsequent (or second) rotor and optionally other subsequent rotors (such as third and fourth rotors). Each rotor rotates about a different substantially horizontal axis with a rotational direction opposite to the rotational direction of the or each adjacent rotor in the sequence. The different horizontal axes are arranged such that melt which is poured on to the top rotor is thrown in sequence on to the peripheral surface of the or each subsequent rotor, and fibres are thrown off the or each subsequent rotor, and optionally also off the top rotor.

In one embodiment, a cascade spinner or other spinner is arranged to fiberise the melt and the fibres are entrained in air as a cloud of the fibres.

Many fiber forming apparatuses comprise a disc or cup that spins around a substantially vertical axis. It is then conventional to arrange several of these spinners in-line, i.e. substantially in the first direction, for instance as described in GB-A-926,749, U.S. Pat. No. 3,824,086 and WO-A-83/03092.

There is usually a stream of air associated with the one or each fiberising rotor whereby the fibres are entrained in this air as they are formed off the surface of the rotor.

In one embodiment, binder and/or additives is added to the cloud of fibres by known means. The amount of binder and/or additive may be the same for each spinner or it may be different.

In one embodiment, a hydrocarbon oil may be added into the cloud of fibres.

As used herein, the term "collected web" is intended to include any mineral fibres that have been collected together on a surface, i.e. they are no longer entrained in air, e.g. the fibrerised mineral fibres, granulate, tufts or recycled web waste. The collected web could be a primary web that has been formed by collection of fibres on a conveyor belt and provided as a starting material without having been cross-lapped or otherwise consolidated.

Alternatively, the collected web could be a secondary web that has been formed by crosslapping or otherwise consolidating a primary web. Preferably, the collected web is a primary web.

The particulate endothermic material may be added to the collected web at any suitable stage in the production.

In one embodiment the mixing of the binder with the mineral fibres is done after the provision of the collected web in the following steps:

subjecting the collected web of mineral fibres to a disentanglement process,
suspending the mineral fibres in a primary air flow,
mixing binder composition with the mineral fibres before, during or after the disentanglement process to form a mixture of mineral fibres and binder.

A method of producing a mineral wool product comprising the process step of disentanglement is described in EP10190521.

In one embodiment, the disentanglement process comprises feeding the collected web of mineral fibres from a duct with a lower relative air flow to a duct with a higher relative air flow. In this embodiment, the disentanglement is believed to occur, because the fibres that enter the duct with the higher relative air flow first are dragged away from the subsequent fibres in the web. This type of disentanglement is particularly effective for producing open tufts of fibres, rather than the compacted lumps that can result in an uneven distribution of materials in the product.

According to a particularly preferred embodiment, the disentanglement process comprises feeding the collected web to at least one roller which rotates about its longitudinal axis and has spikes protruding from its circumferential surface. In this embodiment, the rotating roller will usually also contribute at least in part to the higher relative air flow. Often, rotation of the roller is the sole source of the higher relative air flow.

In preferred embodiments, the mineral fibres and optionally the binder are fed to the roller from above. It is also preferred for the disentangled mineral fibres and optionally the binder to be thrown away from the roller laterally from the lower part of its circumference. In the most preferred embodiment, the mineral fibres are carried approximately 180 degrees by the roller before being thrown off.

The binder may be mixed with the mineral fibres before, during or after the disentanglement process. In some embodiments, it is preferred to mix the binder with the fibres prior to the disentanglement process. In particular, the fibres can be in the form of an uncured collected web containing binder.

It is also feasible that the binder be pre-mixed with a collected web of mineral fibres before the disentanglement process. Further mixing could occur during and after the disentanglement process. Alternatively, it could be supplied to the primary air flow separately and mixed in the primary air flow.

The mixture of mineral fibres and binder is collected from the primary air flow by any suitable means. In one embodiment, the primary air flow is directed into the top of a cyclone chamber, which is open at its lower end and the mixture is collected from the lower end of the cyclone chamber.

The mixture of mineral fibres and binder is preferably thrown from the disentanglement process into a forming chamber.

Having undergone the disentanglement process, the mixture of mineral fibres and binder is collected, pressed and cured. Preferably, the mixture is collected on a foraminous conveyor belt having suction means positioned below it.

In a preferred method according to the invention, the mixture of binder and mineral fibres, having been collected, is pressed and cured.

In a preferred method according to the invention, the mixture of binder and mineral fibres, having been collected, is scalped before being pressed and cured.

The method may be performed as a batch process, however according to an embodiment the method is performed at a mineral wool production line feeding a primary or secondary mineral wool web into the fibre separating process, which provides a particularly cost efficient and versatile method to provide composites having favourable mechanical properties and thermal insulation properties in a wide range of densities.

At the same time, because of the curing at ambient temperature, the likelihood of uncured binder spots is strongly decreased.

The particulate endothermic material may be added to the web at any suitable stage in the production.

Curing

The web is cured by a chemical and/or physical reaction of the binder components.

In one embodiment, the curing takes place in a curing device.

In one embodiment the curing is carried out at temperatures from 5 to 95° C., such as 5 to 80° C., such as 5 to 60° C., such as 8 to 50° C., such as 10 to 40° C.

In one embodiment the curing takes place in a conventional curing oven for mineral wool production operating at a temperature of from 5 to 95° C., such as 5 to 80° C., such as 10 to 60° C., such as 20 to 40° C.

The curing process may commence immediately after application of the binder to the fibres. The curing is defined as a process whereby the binder composition undergoes a physical and/or chemical reaction which in case of a chemical reaction usually increases the molecular weight of the compounds in the binder composition and thereby increases the viscosity of the binder composition, usually until the binder composition reaches a solid state.

In one embodiment the curing process comprises crosslinking and/or water inclusion as crystal water.

In one embodiment the cured binder contains crystal water that may decrease in content and raise in content depending on the prevailing conditions of temperature, pressure and humidity.

In one embodiment the curing process comprises a drying process.

In a preferred embodiment, the curing of the binder in contact with the mineral fibers takes place in a heat press.

The curing of a binder in contact with the mineral fibers in a heat press has the particular advantage that it enables the production of high-density products.

In one embodiment the curing process comprises drying by pressure. The pressure may be applied by blowing air or gas through/over the mixture of mineral fibres and binder. The blowing process may be accompanied by heating or cooling or it may be at ambient temperature.

In one embodiment the curing process takes place in a humid environment.

The humid environment may have a relative humidity RH of 60-99%, such as 70-95%, such as 80-92%. The curing, in a humid environment may be followed by curing or drying to obtain a state of the prevalent humidity.

In one embodiment the curing is performed in oxygen-depleted surroundings.

Without wanting to be bound by any particular theory, the applicant believes that performing the curing in an oxygen-depleted surrounding is particularly beneficial when the binder composition includes an enzyme because it increases the stability of the enzyme component in some embodiments, in particular of the transglutaminase enzyme, and thereby improves the crosslinking efficiency. In one embodiment, the curing process is therefore performed in an inert atmosphere, in particular in an atmosphere of an inert gas, like nitrogen.

In some embodiments, in particular in embodiments in which the binder composition includes phenolics, in particular tannins oxidizing, agents can be added. Oxidising agents as additives can serve to increase the oxidising rate of the phenolics in particular tannins. One example is the enzyme tyrosinase which oxidizes phenols to hydroxyphenols/quinones and therefore accelerates the binder forming reaction.

In another embodiment, the oxidising agent is oxygen, which is supplied to the binder.

In one embodiment, the curing is performed in oxygen-enriched surroundings.

The mineral wool product can be in any conventional configuration, for instance a mat or slab, and can be cut and/or shaped before, during or after curing of the binder.

EXAMPLES

In the following examples, several binders which fall under the definition used in the present invention were prepared and compared to binders according to the prior art.
Test Methods for Binder Compositions According to the Prior Art The following properties were determined for the binders according the prior art.

Reagents

Silane (Momentive VS-142) was supplied by Momentive and was calculated as 100% for simplicity. Ali other components were supplied in, high purity by Sigma-Aldrich and were assumed anhydrous for simplicity unless stated otherwise.

Binder Component Solids Content—Definition

The content of each of the components in a given binder solution before curing is based on the anhydrous mass of the components. The following formula can be used:

$$\text{Binder component solids content (\%)} = \frac{\text{binder component } A \text{ solids } (g) + \text{binder component } B \text{ solids } (g) + -}{\text{total weight of mixture } (g)} \times 100\%$$

Binder Solids—Definition and Procedure

The content of binder after curing is termed "binder solids".

Disc-shaped stone wool samples (diameter: 5 cm; height 1 cm) were cut out of stone wool and heat-treated at 580° C. for at least 30 minutes to remove all organics. The solids of the binder mixture (see below for mixing examples) were measured by distributing a sample of the binder mixture (approx. 2 g) onto a heat treated stone wool disc in a tin foil container. The weight of the tin foil container containing the stone wool disc was weighed before and directly after addition of the binder mixture. Two such binder mixture loaded stone wool discs in tin foil containers were produced and they were then heated at 200° C. for 1 hour. After cooling and storing at room temperature for 10 minutes, the samples were weighed and the binder solids were calculated as an average of the two results. A binder with the desired binder solids could then be produced by diluting with the required amount of water and 10% aq. silane (Momentive VS-142).

Reaction Loss—Definition

The reaction loss is defined as the difference between the binder component solids content and the binder solids.
Mechanical Strength Studies (Bar Tests)—Procedure The mechanical strength of the binders was tested in a bar test. For each binder, 16 bars were manufactured from a mixture of the binder and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A 15% binder solids binder solution containing 0.5% silane (Momentive VS-142) of binder solids was obtained as described above under "binder solids". A sample of this binder solution (16.0 g) was mixed well with shots (80.0 g). The resulting mixture was then filled into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). The mixtures placed in the slots were then pressed hard with a suitably sized flat metal bar to generate even bar surfaces. 16 bars from each binder were made in this fashion. The resulting bars were then cured at 200° C. for 1 h.

After cooling to room temperature, the bars were carefully taken out of the containers. Five of the bars were aged in a water bath at 80° C. for 3 h or in an autoclave (15 min/120° C. 1.2 bar).

After drying for 1-2 days, the aged bars as well as five unaged bars were broken in a 3 point bending test (test speed: 10.0 min/min; rupture level: 50%; nominal strength: 30 N/mm2; support distance: 40 mm; max deflection 20 mm; nominal e-module 10000 N/mm2) on a Bent Tram machine to investigate their mechanical strengths. The bars were placed with the "top face" up (i.e. the face with the dimensions length=5.6 cm, width=2.5 cm) in the machine.
Loss of Ignition (LOI) of Bars The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI(\%) = \frac{\text{Weight of bars before heat treatment } (g) - \text{Weight of bars after heat treatment } (g)}{\text{Weight of bars before heat treatment } (g)} \times 100\%$$

Water Absorption Measurements

The water absorption of the binders was measured by weighing three bars and then submerging the bars in water (approx. 250 mL) in a beaker (565 mL, bottom Ø=9.5 cm; top Ø=10.5 cm; height=7.5 cm) for 3 h or 24 h. The bars were placed next to each other on the bottom of the beaker with the "top face" down (i.e. the face with the dimensions length=5.6 cm, width=2.5 cm). After the designated amount of time, the bars were lifted up one by one and allowed to drip off for one minute. The bars were held (gently) with the length side almost vertical so that the droplets would drip from a corner of the bar. The bars were then weighed and the water absorption was calculated using the following formula:

$$Waterabs(\%) = \frac{\text{Weight of bars after water treatment }(g) - }{\text{Weight of bars before water treatment }(g)} \times 100\%$$

Reference Binder Compositions from the Prior Art

Binder Example, Reference Binder A (Phenol-Formaldehyde Resin Modified with Urea, a PUF-Resol)

A phenol-formaldehyde resin is prepared by reacting 37% aq. formaldehyde (606 g) and phenol (189 g) in the presence of 46% aq, potassium hydroxide (25.5 g) at a reaction temperature of 84° C. preceded by a heating rate of approximately 1° C. per minute. The reaction is continued at 84° C. until the acid tolerance of the resin is 4 and most of the phenol is converted. Urea (241 g) is then added and the mixture is cooled.

The acid tolerance (AT) expresses the number of times a given volume of a binder can be diluted with acid without the mixture becoming cloudy (the binder precipitates). Sulfuric acid is used to determine the stop criterion in a binder, production and an acid tolerance lower than 4 indicates the end of the binder reaction. To measure the AT, a titrant is produced from diluting 2.5 mL conc. sulfuric acid (>99%) with 1 L ion exchanged water. 5 mL of the binder to be investigated is then titrated at room temperature with this titrant while keeping the binder in motion by manually shaking it; if preferred, use a magnetic stirrer and a magnetic stick. Titration is continued until a slight cloud appears in the binder, which does not disappear when the binder is shaken.

The acid tolerance (AT) is calculated by dividing the amount of acid used for the titration (mL) with the amount of sample (mL):

AT=(Used titration volume (mL))/(Sample volume (mL))

Using the urea-modified phenol-formaldehyde resin obtained, a binder is made by addition of 25% aq. ammonia (90 mL) and ammonium sulfate (13.2 g) followed by water (1.30 kg). The binder solids were then measured as described above and the mixture was diluted with the required amount of water and silane (Momentive VS-142) for mechanical strength studies (15% binder solids solution, 0.5% silane of binder solids).

Test Methods for Binder Compositions Used in the Present Invention and Reference Binders The following properties were determined for the binders used in the present invention and reference binders.

Reagents

Speisegelatines, type A, porcine (120 bloom and 180 bloom) were obtained from Gelita AG. Tannorouge chestnut tree tannin was obtained from Brouwland bvba. TI Transglutaminase formula was obtained from Modernist Pantry. Coconut oil, hemp oil, olive oil, rapeseed oil and sunflower oil were obtained from Urtekram International A/S. Linseed oil was obtained from Borup Kemi I/S. Medium gel strength gelatin from porcine skin (170-195 g Bloom), sodium hydroxide, tung oil and all other components were obtained from Sigma-Aldrich. Unless stated otherwise, these components were assumed completely pure and anhydrous.

Binder Component Solids Content—Definition

The content of each of the components in a given binder solution before curing is based on the anhydrous mass of the components. The following formula can be used:

$$\text{Binder component solids content }(\%) = \frac{\text{binder component }A\text{ solids }(g) + \text{binder component }B\text{ solids }(g) + -}{\text{total weight of mixture }(g)} \times 100\%$$

Mechanical Strength Studies (Bar Tests)—Procedure

The mechanical strength of the binders was tested in a bar test. For each, binder, 16-20 bars were manufactured from a mixture of the binder and stone wool shots from the stone wool spinning production. The shots are particles which have the same melt composition as the stone wool fibers, and the shots are normally considered a waste product from the spinning process. The shots used for the bar composition have a size of 0.25-0.50 mm.

A binder solution with approx. 15% binder component solids was obtained as described in the examples below. A sample of the binder solution (16.0 g) was mixed well with shots (80.0 g; pre-heated to 40° C. when used in combination with comparatively fast setting binders). The resulting mixture was then filled into four slots in a heat resistant silicone form for making small bars (4×5 slots per form; slot top dimension: length=5.6 cm, width=2.5 cm; slot bottom dimension: length=5.3 cm, width=2.2 cm; slot height=1.1 cm). During the manufacture of each bar, the mixtures placed in the slots were pressed as required and then evened out with a plastic spatula to generate an even bar surface. 16-20 bars from each binder were made in this fashion. The resulting bars were then cured at room temperature for 1-2 days. The bars were then carefully taken out of the containers, turned upside down and left for a day at room temperature to cure completely. Five of the bars were aged in a water bath at 80° C. for 3 h or in an autoclave (15 min/120° C./1.2 bar).

After drying for 1-2 days, the aged bars as well as five unaged bars were broken in a 3 point bending test (test speed: 10.0 mm/min; rupture level: 50%; nominal strength: 30 N/mm2; support distance: 40 mm; max deflection 20 mm; nominal e-module 10000 N/mm2) on a Bent Tram machine to investigate their mechanical strengths. The bars were placed with the "top face" up (i.e. the face with the dimensions length=5.6 cm, width=2.5 cm) in the machine.

Loss of Ignition (LOI) of Bars

The loss of ignition (LOI) of bars was measured in small tin foil containers by treatment at 580° C. For each measurement, a tin foil container was first heat-treated at 580° C. for 15 minutes to remove all organics. The tin foil container was allowed to cool to ambient temperature, and was then weighed. Four bars (usually after being broken in the 3 point bending test) were placed into the tin foil container and the ensemble was weighed. The tin foil container containing bars was then heat-treated at 580° C. for 30 minutes, allowed to cool to ambient temperature, and finally weighed again. The LOI was then calculated using the following formula:

$$LOI(\%) = \frac{\text{Weight of bars before heat treatment }(g) - \text{Weight of bars after heat treatment }(g)}{\text{Weight of bars before heat treatment }(g)} \times 100\%$$

Water Absorption Measurements

The water absorption of the binders was measured by weighing three bars and then submerging the bars in water (approx. 250 mL) in a beaker (565 mL, bottom Ø=9.5 cm; top Ø=10.5 cm height=7.5 cm) for 3 h or 24 h. The bars were placed next to each other on the bottom of the beaker with the "top face" down (i.e. the face with the dimensions length=5.6 cm, width=2.5 cm). After the designated amount of time, the bars were lifted up one by one and allowed to drip off for one minute. The bars were held (gently) with the length side almost vertical so that the droplets would drip from a corner of the bar. The bars were then weighed and the water absorption was calculated using the following formula:

$$Waterabs(\%) = \frac{\text{Weight of bars after water treatment (g)} - \text{Weight of bars before water treatment (g)}}{\text{Weight of bars before water treatment (g)}} \times 100\%$$

Binder Compositions Used in the Present Invention and Reference Binders

Binder Example, Entry B

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 120 bloom, 12.0 g) in water (68.0 g) was stirred at 50° C. for approx. 15-30 min until a clear solution was obtained (pH 5.0). 1M NaOH (4.37 g) was then added (pH 9.1) followed by a portion of the above chestnut tree tannin solution (5.40 g thus efficiently 1.20 g chestnut tree tannin). After stirring for 1-2 minutes further at 50° C., the resulting brown mixture (pH 9.1) was used in the subsequent experiments.

Binder Example, Entry 3

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 120 bloom, 10.0 g) in water (56.7 g) was stirred at 50° C. for approx. 15-30 min until a clear solution was obtained (pH 5.1). 1M NaOH (4.00 g) was added (pH 9.3) followed by a portion of the above chestnut tree tannin solution (4.50 g; thus efficiently 1.00 g chestnut tree tannin). Coconut oil (0.65 g) was then added under vigorous stirring. After stirring vigorously for approx. 1 minute at 50° C., the stirring speed was slowed down again and the resulting brown mixture (pH 9.3) was used in the subsequent experiments.

Binder Example, Entry 5

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 120 bloom, 10.0 g) in water (56.7 g) was stirred at 50° C. for approx. 15-30 min until a clear solution was obtained (pH 4.8). 1M NaOH (4.00 g) was added (pH 9.2) followed by a portion of the above chestnut tree tannin solution (4.50 g thus efficiently 1.00 g chestnut tree tannin). Linseed oil (0.65 g) was then added under vigorous stirring. After stirring vigorously for approx. 1 minute at 50° C., the stirring speed was slowed down again and the resulting brown mixture (pH 9.2) was used in the subsequent experiments.

Binder Example, Entry 6

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 120 bloom, 10.0 g) in water (56.7 g) was stirred at 50° C. for approx. 15-30 min until, a clear solution was obtained (pH 4.8). 1M NaOH (4.00 g) was added (pH 9.2) followed by a portion of the above chestnut tree tannin solution (4.50 g; thus efficiently 1.00 g chestnut tree tannin). Olive oil (0.65 g) was then added under vigorous stirring. After stirring vigorously for approx. 1 minute at 50° C., the stirring speed was slowed down again and the resulting brown mixture (pH 9.1) was used in the subsequent experiments.

Binder Example, Entry 9

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 120 bloom, 10.0 g) in water (567 g) was stirred at 50° C. for approx. 15-30 min until a clear solution was obtained (pH 4.8), 1M NaOH (4.00 g) was added (pH 9.3) followed by a portion of the above chestnut tree tannin solution (4.50 g; thus efficiently 1.00 g chestnut tree tannin). Tung oil (0.16 g) was then added under vigorous stirring. After stirring vigorously for approx. 1 minute at 50° C., the stirring speed was slowed down again and the resulting brown mixture (pH 9.4) was used in the subsequent experiments.

Binder Example, Entry 11

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 120 bloom, 10.0 g) in water (56.7 g) was stirred at 50° C. for approx. 15-30 min until a clear solution was obtained (pH 5.0). 1M NaOH (4.00 g) was added (pH 9.1) followed by a portion of the above chestnut tree tannin solution (4.50 g; thus efficiently 1.00 g chestnut tree tannin). Tung oil (1.13 g) was then added under vigorous stirring. After stirring vigorously for approx. 1 minute at 50° C., the stirring speed was slowed down again and the resulting brown mixture (pH 9.1) was used in the subsequent experiments.

Binder Example, Entry C

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 180 bloom, 12.0 g) in water (68.0 g) was stirred at 50° C. for approx. 15-30 min until a clear solution was obtained (pH 5.0). 1M NaOH (3.81 g) was then added (pH 9.1) followed by a portion of the above chestnut tree tannin solution (5.40 g; thus efficiently 1.20 g chestnut tree tannin). After stirring for 1-2 minutes further at 50° C., the resulting brown mixture (pH 9.3) was used in the subsequent experiments.

Binder Example, Entry 12

To 1M NaOH (15.75 g) stirred at room temperature was added chestnut tree tannin (4.50 g). Stirring was continued at room temperature for 5-10 min further, yielding a deep red-brown solution.

A mixture of gelatin (Speisegelatine, type A, porcine, 180 bloom, 10.0 g) in water (56.7 g) was stirred at 50° C. for approx. 15-30 min until a clear solution was obtained (pH 5.0). 1M NaOH (3.28 g) was added (pH 9.2) followed by a portion of the above chestnut tree tannin solution (4.50 g; thus efficiently 1.00 g chestnut tree tannin). Tung oil (0.65 g) was then added under vigorous stirring. After stirring vigorously for approx. 1 minute at 50° C., the stirring speed was slowed down again and the resulting brown mixture (pH 9.1) was used in the subsequent experiments.

Binder Example, Entry D

A mixture of gelatin (Porcine skin, medium gel strength, 12.0 g) in water (62.0 g) was stirred at 37° C. for approx. 15-30 min until a clear solution was obtained (pH 5.5). A solution of TI transglutaminase (0.60 g) in water (6.0 g) was then added. After stirring for 1-2 minutes further at 37° C., the resulting tan mixture (pH 5.5) was used in the subsequent experiments.

Binder Example, Entry 13

A mixture of gelatin (Porcine skin, medium gel strength, 12.0 g) in water (62.0 g) was stirred at 37° C. for approx. 15-30 min until a clear solution was obtained (pH 5.5). A solution of TI transglutaminase (0.60 g) in water (6.0 g) was added. Linseed oil (0.63 g) was then added under more vigorous stirring. After stirring more vigorously for approx. 1 minute at 37° C., the stirring speed was slowed down again and the resulting tan mixture (pH 5.5) was used in the subsequent experiments.

Binder Example, Entry E

A mixture of gelatin (Speisegelatine, type A, porcine, 120 bloom, 12.0 g) in water (68.0 g) was stirred at 50° C. for approx. 15-30 min until a clear solution was obtained (pH 4.8). 1M NaOH (4.42 g) was then added. After stirring for 1-2 minutes further at 50° C., the resulting tan mixture (pH 9.0) was used in the subsequent experiments, Binder Example, Entry 14

A mixture of gelatin (Speisegelatine, type A, porcine, 120 bloom, 10.0 g) in water (56.7 g) was stirred at 50° C. for approx. 15-30 min until a clear solution was obtained (pH 5.1). 1M NaOH (4.00 g) was added (pH 9.4). Tung oil (0.65 g) was then added under vigorous stirring. After stirring vigorously for approx. 1 minute at 50° C., the stirring speed was slowed down again and the resulting tan mixture (pH 9.1) was used in the subsequent experiments.

Binder Example, Entry 15

A mixture of gelatin (Speisegelatine, type A, porcine, 120 bloom, 10.0 g) in water (56.7 g) was stirred at 50° C. for approx. 15-30 min until a clear solution was obtained (pH 5.1). 1M NaOH (4.00 g) was added (pH 9.3). Tung oil (1.13 g) was then added under vigorous stirring. After stirring vigorously for approx. 1 minute at 50° C., the stirring speed was slowed down again and the resulting tan mixture (pH 9.1) was used in the subsequent experiments.

TABLE 1-1

| Reference binder according to the prior art | |
|---|---|
| Example | A |
| Binder properties | |
| Binder solids (%) | 15.0 |
| Reaction loss (%) | 28.5 |
| pH | 9.6 |
| Bar curing conditions | |
| Temperature (° C./1 h) | 200 |
| Bar properties | |
| Mechanical strength, unaged (kN) | 0.39 |
| Mechanical strength, water bath aged (kN) | 0.28 |

TABLE 1-1-continued

| Reference binder according to the prior art | |
|---|---|
| Example | A |
| Mechanical strength, autoclave aged (kN) | 0.28 |
| LOI, unaged (%) | 2.8 |
| LOI, water bath aged (%) | 2.8 |
| Water absorption, 3 h (%) | 4 |
| Water absorption, 24 h (%) | 8 |

TABLE 1-2

Hydrocolloid, crosslinker, mineral oil or fatty acid ester of glycerol

| | Example | | | | | | |
|---|---|---|---|---|---|---|---|
| | B | 1 | 2 | 3 | 4 | 5 | 6 |
| Binder composition Hydrocolloid (%-wt.) | | | | | | | |
| Gelatin, Speisegelatine, 120 bloom | 100 | 100 | 100 | 100 | 100 | 100 | 100 |
| Gelatin, Speisegelatine, 180 bloom | — | — | — | — | — | — | — |
| Cross:linker (%-wt.) [a] | | | | | | | |
| Chestnut tree tannin | 10 | 10 | 10 | 10 | 10 | 10 | 10 |
| Fatty acid ester of glycerol (%-wt.) [a] | | | | | | | |
| Mineral oil | — | 1.6 | 6.5 | — | — | — | — |
| Coconut oil (iodine number 7 to 10) | — | — | — | 6.5 | — | — | — |
| Hemp oil (iodine number 140 to 170) | — | — | — | — | 6.5 | — | — |
| Linseed oil (iodine number 136 to 178) | — | — | — | — | — | 6.5 | — |
| Olive oil (iodine number 80 to 88) | — | — | — | — | — | — | 6.5 |
| Base (%-wt.) [b] | | | | | | | |
| Sodium hydroxide | 2.5 | 2.6 | 2.5 | 2.5 | 2.5 | 2.5 | 2.5 |
| Binder mixing and bar manufacture | | | | | | | |
| Binder component solids content (%) | 15.1 | 15.2 | 15.7 | 15.7 | 15.7 | 15.7 | 15.7 |
| pH of binder mixture | 9.1 | 9.1 | 9.1 | 9.3 | 9.1 | 9.2 | 9.1 |
| Curing temperature (° C.) | rt | rt | rt | rt | rt | rt | rt |
| Bar properties | | | | | | | |
| Mechanical strength, unaged (kN) | 0.22 | 0.19 | 0.18 | 0.31 | 0.31 | 0.34 | 0.34 |
| Mechanical strength, aged (kN) | 0.17 | 0.12 | 0.12 | 0.25 | 0.24 | 0.30 | 0.28 |
| LOI, unaged (%) | 2.9 | 2.9 | 2.9 | 3.0 | 3.0 | 3.0 | 3.0 |
| LOI, water bath aged (%) | 2.6 | 2.6 | 2.7 | 2.8 | 2.8 | 2.8 | 2.8 |
| Water absorption, 3 h (%) | 16 | 18 | 16 | 10 | 10 | 9 | 10 |
| Water absorption, 24 h (%) | 31 | 31 | 32 | 23 | 24 | 23 | 22 |

[a] Of hydrocolloid.
[b] Of hydrocolloid + crosslinker.

TABLE 1-3

Hydrocolloid, crosslinker, fatty acid ester of glycerol

| | Example | | | | | | | |
|---|---|---|---|---|---|---|---|---|
| | B | 7 | 8 | 9 | 10 | 11 | C | 12 |
| Binder composition Hydrocolloid (%-wt.) | | | | | | | | |
| Gelatin, Speisegelatine, 120 bloom | 100 | 100 | 100 | 100 | 100 | 100 | — | — |
| Gelatin, Speisegelatine, 180 bloom | — | — | — | — | — | — | 100 | 100 |
| Crosslinker (%-wt.) [a] | | | | | | | | |
| Chestnut tree tannin | 10 | 10 | 10 | 10 | 10 | 10 | 10 | 10 |
| Fatty acid ester of glycerol (%-wt.) [a] | | | | | | | | |
| Rapeseed oil (iodine number 94 to 120) | — | 6.5 | — | — | — | — | — | — |
| Sunflower oil (iodine number 118 to 144) | — | — | 6.5 | — | — | — | — | — |
| Tung oil (iodine number 163 to 173) | — | — | — | 1.6 | 6.5 | 11.3 | — | 6.5 |
| Base (%-wt.) [b] | | | | | | | | |
| Sodium hydroxide | 2.5 | 2.5 | 2.5 | 2.6 | 2.5 | 2.4 | 2.3 | 2.2 |
| Binder mixing and bar manufacture | | | | | | | | |
| Binder component solids content (%) | 15.1 | 15.7 | 15.7 | 15.2 | 15.7 | 16.3 | 15.1 | 15.9 |
| pH of binder mixture | 9.1 | 9.1 | 9.2 | 9.4 | 9.1 | 9.1 | 9.3 | 9.1 |
| Curing temperature (° C.) | rt | rt | rt | rt | rt | rt | rt | rt |
| Bar properties | | | | | | | | |
| Mechanical strength, unaged (kN) | 0.22 | 0.28 | 0.26 | 0.29 | 0.32 | 0.28 | 0.24 | 0.37 |
| Mechanical strength, aged (kN) | 0.17 | 0.25 | 0.21 | 0.22 | 0.22 | 0.21 | 0.17 | 0.34 |
| LOI, unaged (%) | 2.9 | 2.9 | 3.0 | 2.9 | 3.0 | 3.1 | 2.9 | 3.0 |
| LOI, water bath aged (%) | 2.6 | 2.8 | 2.8 | 2.7 | 2.9 | 3.0 | 2.8 | 2.9 |
| Water absorption, 3 h (%) | 16 | 11 | 10 | 11 | 8 | 8 | 13 | 9 |
| Water absorption, 24 h (%) | 31 | 25 | 24 | 24 | 23 | 20 | 25 | 22 |

[a] Of hydrocolloid.
[b] Of hydrocolloid + crosslinker.

TABLE 1-4

Hydrocolloid, crosslinker, fatty acid ester of glycerol

| Example | D | 13 | E | 14 | 15 |
|---|---|---|---|---|---|
| Binder composition Hydrocolloid (%-wt.) | | | | | |
| Gelatin (porcine skin), medium gel strength | 100 | 100 | — | — | — |
| Gelatin, Speisegelatine, 120 bloom | — | — | 100 | 100 | 100 |
| Crosslinker (%-wt.) [a] | | | | | |
| TI transglutaminase | 5 | 5 | — | — | — |
| Fatty acid ester of glycerol (%-wt.) [a] | | | | | |
| Tung oil (iodine number 183 to 173) | — | — | — | 6.5 | 11.3 |
| Linseed oil (iodine number 136 to 178) | — | 5.3 | — | — | — |
| Base (%-wt.) [b] | | | | | |
| Sodium hydroxide | — | — | 1.4 | 1.5 | 1.5 |
| Binder mixing and bar manufacture | | | | | |
| Binder component solids content (%) | 15.6 | 16.3 | 14.4 | 15.1 | 15.7 |
| pH of binder mixture | 5.5 | 5.5 | 9.0 | 9.1 | 9.0 |
| Curing temperature (° C.) | rt | rt | rt | rt | rt |
| Bar properties | | | | | |
| Mechanical strength, unaged (kN) | 0.28 | 0.29 | 0.16 | 0.22 | 0.19 |
| Mechanical strength, water bath aged (kN) | 0.20 | 0.20 | — | — | — |
| Mechanical strength, autoclave aged (kN) | — | — | 0.16 | 0.28 | 0.24 |
| LOI, unaged (%) | 3.0 | 3.2 | 2.7 | 3.0 | 3.1 |
| LOI, water bath aged (%) | 2.7 | 2.8 | — | — | — |
| Water absorption, 3 h (%) | 6 | 5 | — | — | — |
| Water absorption, 24 h (%) | 9 | 10 | — | — | — |

[a] Of hydrocolloid.
[b] Of hydrocolloid + crosslinker.

Experiments

The fire properties of a stone wool fibrous product according to the invention, but without endothermic material, were tested. Comparative tests have been performed testing a product sample according to the present invention, but without endothermic material, and a reference product sample made of stone wool fibres and a conventional binder (phenol-formaldehyde resin modified with urea). The samples are as apparent in the following of similar properties.

Figure 2:
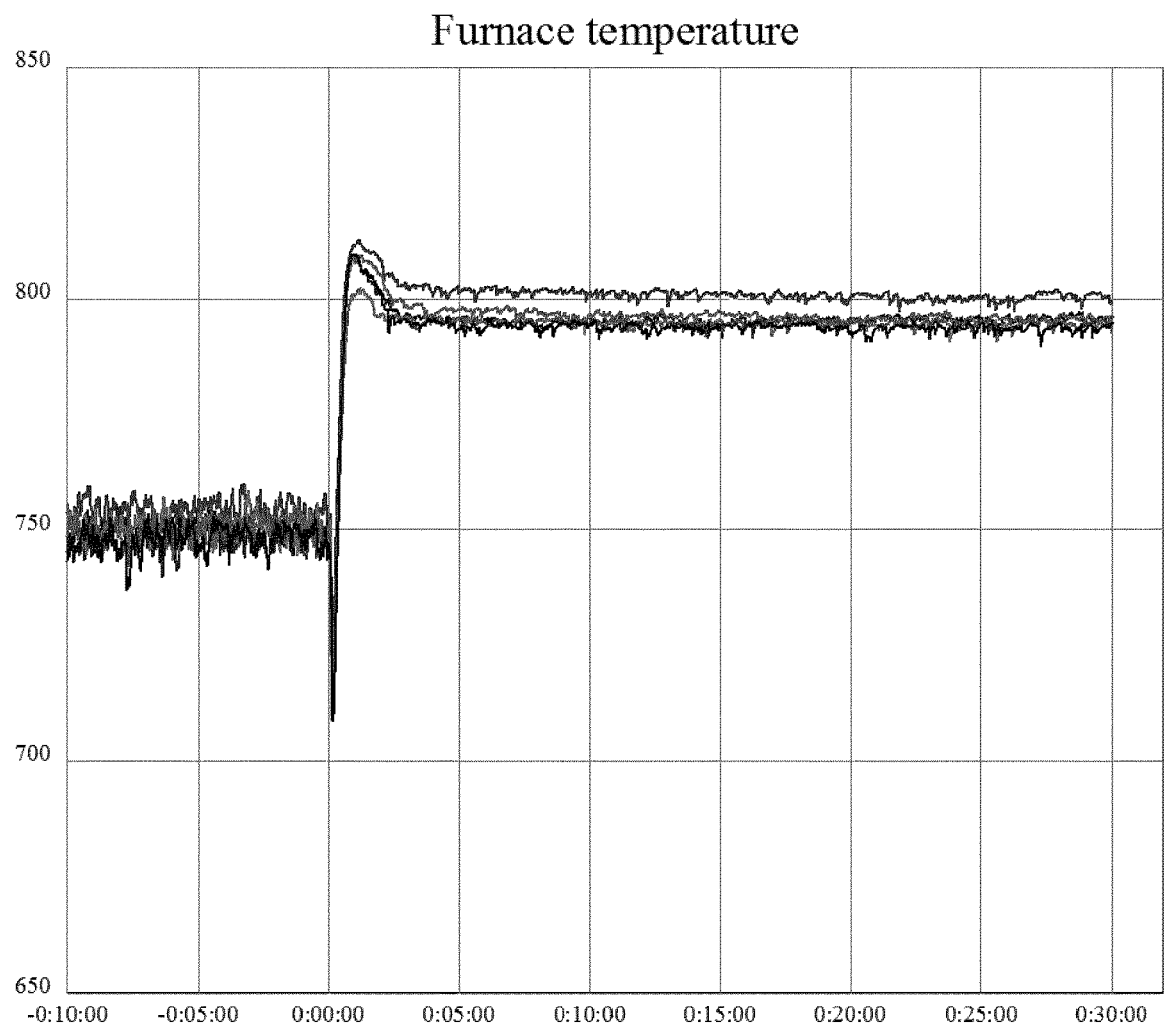
FIG. 2 shows a graph for a reference product (without endothermic material)

Tests according to EN-ISO 1182-2010 have been performed. The test results are shown in FIGS. 1 and 2, where the graphs in FIG. 1 are for the product according to the present invention (without endothermic material) and the graphs in FIG. 2 are for a reference product (without endothermic material). The product according to the invention has an average density of 78.9 kg/m$^3$ and a LOI (loss of ignition) of 3.1%. The reference product has an average density of 80.6 kg/m$^3$ and a LOI (loss of ignition) of 3.7%.

In FIGS. 1 and 2, the x-axis shows the time and the Y-axis is the temperature.

The tests are performed by heating an oven to 750° C. having a steady airflow through it. Then the test sample (relatively small piece) is lowered into the oven causing a drop of measured temperature; the sample is "cold". The measured temperature then increases to a new stable temperature of 800° C. (not because more heat is supplied to the oven, but because the sample "blocks" some of the airstream in the oven, so that the air flows faster and an increased temperature is measured). Tests with any sample will show this temperature increase from 750° C. to 800° C. The relevant part of the test result is how the curve behaves between the temperature change.

The test result shows that the sample product according to the invention (see FIG. 1) causes a slower increase in temperature than the reference product (see FIG. 2): the slope is less vertical and the position where the curve crosses the 800° C. is later. This indicates that the product according to the invention takes up or "eats" more energy than the reference sample.

Another relevant observation is the "overheating", where the product according to the invention shows almost no overheating (in average measured to 2.6° C.) (see Figure. 1), whereas the reference, product shows a substantial overheating (in average measured to 12.6° C.) (see FIG. 2). The overheating is related to the burning off of organic substance (i.e. binder) in the sample product. A conventional product like the reference sample product always shows such overheating. It is believed that the sample product according to the invention shows almost no overheating because the chemically bound water in the binder "eats" at least some of the energy, when the organic part of the binder is burned off. This may also be what causes the slope of the curve to be less vertical.

Figure 3:
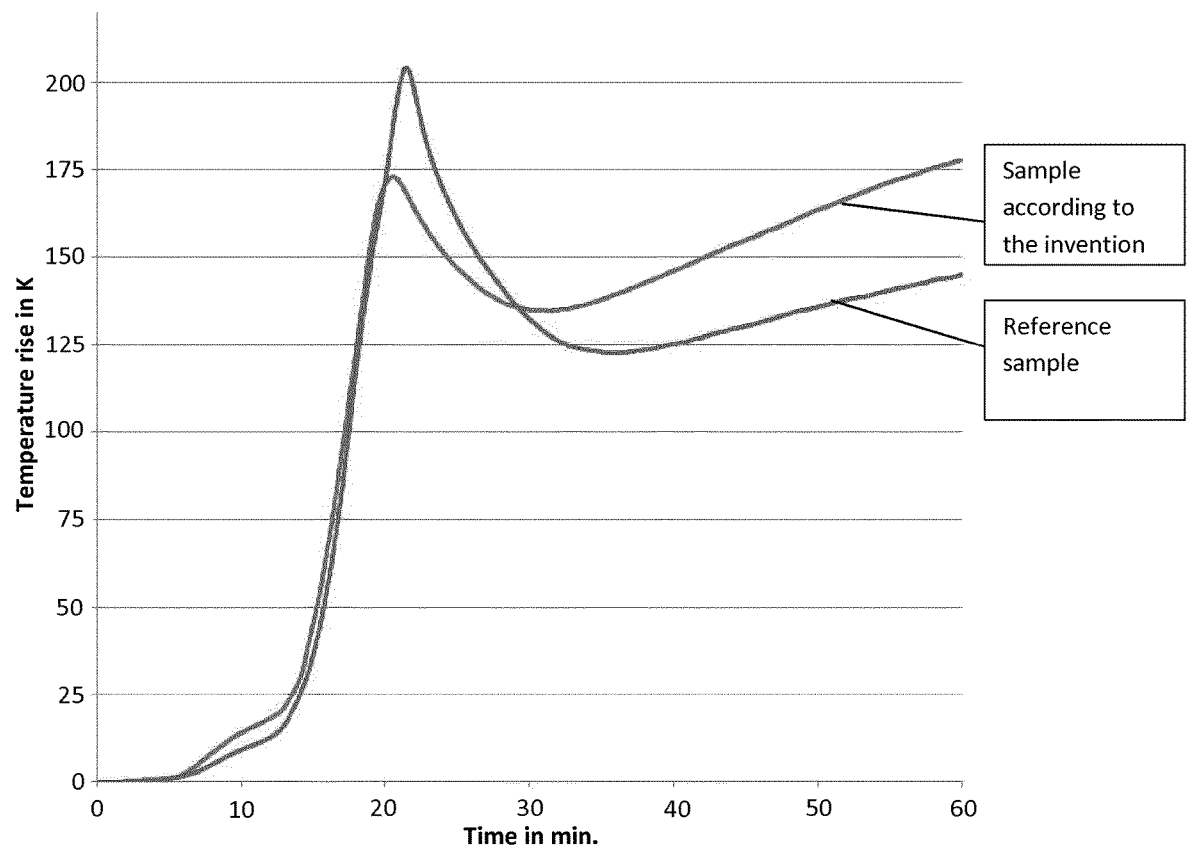
FIG. 3 shows similar sample products as in the tests shown in FIGS. 1 and 2.

In FIG. 3 similar sample products as in the tests shown in FIGS. 1 and 2 are tested for its fire retarding properties.

The product sample according to the present invention is made of stone wool fibres and a binder according to the invention with a thickness of 61 mm and a density of 73.8 kg/m³. The reference sample is made of stone wool fibres and a conventional binder (phenol-formaldehyde resin modified with urea) with a thickness of 61 mm and a density of 76.8 kg/m³. Again, both samples are without endothermic material.

The result of this other shows to some degree the same phenomena as in the first test.

The shape of both curves is as expected. In this test the products are heated from one side and the curves show the measured temperatures on the opposite side. The increase until peak indicates heat traveling through the product and the heat originating from burning off of binder in the product. The drop after the peak indicates that there is more contribution from the binder and now it is only the heat from the first side that contributes.

The curves show that the product sample according to the invention has a flower peak temperature and a smaller drop than the reference product sample meaning that the binder contributes less to the heat increase on the second side than for the reference product.

The test also indicates that a mineral wool fire-protecting product according to the invention should have better fire retarding properties than a conventional mineral wool product.

Overall, from the tests it is concluded that the product according to the invention (without endothermic material) satisfies the fire protection properties laid down in the standard so that the product can be classified as Euroclass A1 for reaction to fire.

Furthermore, since the binder used in the fire-protection product according to the invention does not require high temperatures for curing, it is possible to add a wide range of endothermic materials to the product, so that the overall fire-protecting properties might be even better than for conventional mineral wool fire-protecting products.

The invention claimed is:

1. A fire-protecting insulation product comprising:
   air-laid mineral wool fibres;
   a binder, said binder being the result of curing a binder composition comprising:
   at least one hydrocolloid comprising gelatin; and
   a tannin, an enzyme, or both a tannin and an enzyme, wherein:
   the tannin is selected from the group consisting of tannic acid, condensed tannins (proanthocyanidins), hydrolysable tannins, gallotannins, ellagitannins, complex tannins, and tannin originating from one or more of oak, chestnut, staghorn sumac, fringe cups, and combinations thereof; and
   the enzyme is selected from the group consisting of transglutaminase (EC 2.3.2.13), protein disulfide isomerase (EC 5.3.4.1), thiol oxidase (EC 1.8.3.2), polyphenol oxidase (EC 1.14.18.1), lysyl oxidase (EC 1.4.3.13), and peroxidase (EC 1.11.1.7); and
   a particulate endothermic material selected from the group consisting of gypsum, magnesium hydroxide, hydromagnesite, aluminium hydroxide, and aluminium trihydroxide;
   wherein the binder composition is cured at a curing temperature of from 5 to 95° C.;
   wherein the binder composition has a pH of 7 to 10;
   wherein the binder has a 3-point bending strength of at least 0.18 kN, measured in accordance with a Mechanical Strength Bar Test, unaged condition; and
   wherein the fire-protecting insulation product comprises the mineral wool fibres wherein the fibers are blown into a forming chamber and, while airborne and while still hot, are sprayed with the binder composition and randomly deposited as a mat or web onto a traveling conveyor, the randomly deposited mineral wool fibres then being transferred to a curing oven where the binder composition is cured into the binder by air blown through the randomly deposited mineral wool fibres, thereby binding the mineral wool fibres together.

2. The product according to claim 1, wherein the binder further comprises at least one fatty acid ester of glycerol.

3. The product according to claim 1, wherein the particulate endothermic material is distributed evenly within the fire-protecting insulation product.

4. The product according to claim 1, wherein the product has a first and a second face section of a mineral wool fibre portion with a core section of the mineral wool fibre portion therebetween, and wherein the particulate endothermic material is distributed such that there is a higher concentration of endothermic material in the core section of the mineral fibre wool product than in the first and second face sections.

5. The product according to claim 1, further comprising at least a second hydrocolloid selected from the group consisting of pectin, starch, alginate, agar agar, carrageenan, gellan gum, guar gum, gum arabic, locust bean gum, xanthan gum, and cellulose derivatives.

6. The product according to claim 5, wherein the gelatin is present in the binder composition by an amount of 10 to 95 wt. % based on a combined weight of the at least one hydrocolloid and the at least the second hydrocolloid.

7. The product according to claim 5, wherein the at least one hydrocolloid and the at least the second hydrocolloid have complementary charges.

8. The product according to claim 2, wherein the at least one fatty acid ester of glycerol is soured from a plant oil and/or animal oil.

9. The product according to claim 2, wherein the at least one fatty acid ester of glycerol is sourced from a plant-based oil.

10. The product according to claim 2, wherein the at least one fatty acid ester of glycerol is sourced from one or more components selected from the group consisting of linseed oil, olive oil, tung oil, coconut oil, hemp oil, rapeseed oil, and sunflower oil.

11. The product according to claim 2, wherein the at least one fatty acid ester of glycerol is sourced from an animal oil, or fish oil.

12. The product according to claim 2, wherein the at least one fatty acid ester of glycerol is sourced from a plant oil and/or animal oil having a iodine number of $\geq 75$.

13. The product according to claim 2, wherein the at least one fatty acid ester of glycerol is sourced from a plant oil and/or animal oil having a iodine number of $\leq 100$.

14. The product according to claim 2, wherein the content of the fatty acid ester of glycerol is 0.5 to 40, based on dry hydrocolloid basis.

15. The product according to claim 1, wherein a loss on ignition (LOI) is within the range of 0.1 to 25.0% by weight.

16. The mineral wool product according to claim 1, wherein the binder results from the curing of the binder composition at a temperature of less than 95° C.

17. The product according to claim 1, wherein the binder composition is not a thermoset binder composition.

18. The product according to claim 1, wherein the binder composition does not contain a poly(meth)acrylic acid, a salt of a poly(meth)acrylic acid or an ester of a poly(meth)acrylic acid.

19. The product according to claim 1, wherein the binder is formaldehyde-free.

20. The product according to claim 1, wherein the binder composition consists essentially of:

the at least one hydrocolloid;
the tannin, the enzyme, or both the tannin and the enzyme
at least one fatty acid ester of glycerol;
optionally at least one pH-adjuster;
optionally at least one anti-fouling agent;
optionally at least one anti-swelling agent; and
water.

21. The product according to claim 1, wherein the binder is crosslinked.

22. The product according to claim 1, wherein curing the binder composition further comprises increasing the temperature of the binder composition.

23. The product according to claim 1, wherein the density of the fire-protecting insulation product is in the range of 10-1200 kg/m$^3$.

24. The product according to claim 1, wherein the binder composition comprises the enzyme, and wherein the enzyme is catechol oxidase, tyrosine oxidase, or phenoloxidas.

25. The product according to claim 1, wherein the at least one hydrocolloid further comprises a cellulose derivative selected from the group consisting of carboxymethylcellulose, arabinoxylan, cellulose, curdlan, and β-glucan.

26. The product according to claim 1, wherein the air blown through the web is heated air.

27. A method of making the fire-protecting insulation product of claim 1, the method comprising:
blowing mineral wool fibres into a forming chamber and, while airborne and while still hot, spraying the mineral wool fibres with the binder composition;
randomly depositing the mineral wool fibres as the mat or web onto the traveling conveyor;
adding, to the mat or web of randomly deposited mineral wool fibres, the particulate endothermic material;
transferring the mat or web of randomly deposited mineral wool fibres to the curing oven;
curing the binder composition at the curing temperature of from 5 to 95° C. by blowing air through the mat or web of randomly deposited mineral wool fibres, thereby binding the mineral wool fibres together.

* * * * *